US011446262B2

(12) United States Patent
Zucco Sassi Yonezawa Siviglia et al.

(10) Patent No.: US 11,446,262 B2
(45) Date of Patent: *Sep. 20, 2022

(54) NEUROQUIESCENCE—A TREATMENT FOR NEURODEVELOPMENTAL AND NEURODEGENERATIVE BIOELECTRICAL DYSREGULATION AND DEMYELINATION

(71) Applicants: Debora Zucco Sassi Yonezawa Siviglia, Phoenix, AZ (US); Gary Aaron Howard, Eagan, MN (US)

(72) Inventors: Debora Zucco Sassi Yonezawa Siviglia, Phoenix, AZ (US); Gary Aaron Howard, Eagan, MN (US)

(73) Assignees: Debora Zucco Sassi Yonezawa Siviglia, Phoenix, AZ (US); Gary Aaron Howard, Apple Valley, MN (US)

( * ) Notice: Subject to any disclaimer, the term of this patent is extended or adjusted under 35 U.S.C. 154(b) by 120 days.

This patent is subject to a terminal disclaimer.

(21) Appl. No.: 16/935,064

(22) Filed: Jul. 21, 2020

(65) Prior Publication Data

US 2020/0345665 A1 Nov. 5, 2020
US 2022/0226264 A9 Jul. 21, 2022

Related U.S. Application Data

(63) Continuation-in-part of application No. PCT/US2019/063748, filed on Nov. 27, 2019, and a continuation-in-part of application No. 16/698,444, filed on Nov. 27, 2019, now Pat. No. 10,716,792.

(60) Provisional application No. 63/019,714, filed on May 4, 2020, provisional application No. 62/772,811, filed on Nov. 29, 2018.

(51) Int. Cl.
*A61K 31/551* (2006.01)
*A61K 31/137* (2006.01)
*A61K 31/5517* (2006.01)
*A61K 9/00* (2006.01)

(52) U.S. Cl.
CPC ........ *A61K 31/137* (2013.01); *A61K 31/5517* (2013.01); *A61K 9/0019* (2013.01); *A61K 9/0053* (2013.01)

(58) Field of Classification Search
CPC .......................... A61K 31/551; A61K 31/137
USPC .................................................. 514/220, 654
See application file for complete search history.

(56) References Cited

U.S. PATENT DOCUMENTS

| 6,015,557 | A | 1/2000 | Tobinick et al. |
| 6,177,077 | B1 | 1/2001 | Tobinick |
| 6,419,934 | B1 | 7/2002 | Tobinick |
| 6,419,944 | B2 | 7/2002 | Tobinick |
| 6,537,549 | B2 | 3/2003 | Tobinick |
| 6,936,605 | B2 | 8/2005 | March |
| 6,982,089 | B2 | 1/2006 | Tobinick |
| 7,214,658 | B2 | 5/2007 | Tobinick |
| 8,765,125 | B2 | 7/2014 | Skokos |
| 10,716,792 | B2 * | 7/2020 | Howard ............... A61K 9/0019 |
| 2004/0138238 | A1 | 7/2004 | Dhanoa et al. |
| 2008/0103179 | A1 | 5/2008 | Tam et al. |
| 2014/0057885 | A1 | 2/2014 | Reddy |

OTHER PUBLICATIONS

Albrecht et al., "Brain glial activation in fibromyalgia—A multi-site positron emission tomography investigation," Brain, Behavior, and Immunity, 75, 2019, pp. 72-83.
Auerbach et al., "Genetic biomarkers for the risk of seizures in long QT syndrome," American Academy of Neurology, 2016, pp. 1660-1668.
Bakker et al., "Reduction of Hippocampal Hyperactivity Improves Cognition in Amnestic Mild Cognitive Impairment," Neuron, 74, May 10, 2012, pp. 467-474.
Biswas et al., "Neuronal and glial regulation of CNS angiogenesis and barriergenesis," Development, 2020, 147, 13 pages.
Chell et al., "Nutrition-Responsive Glia Control Exit of Neural Stem Cells from Quiescence," Cell, 143, Dec. 23, 2020, pp. 1161-1173.
Dutchen, Stephanie, "Scientists pinpoint neural activity's role in human longevity," The Harvard Gazette, Oct. 16, 2019, 4 pages.
Feng, Yue, "Convergence and Divergence in the Etiology of Myelin Impairment in Psychiatric Disorders and Drug Addiction," Neurochem Res, 2008, 33, pp. 1940-1949.
Heard et al., "Sedation and Analgesia," Pediatric Critical Care (Fourth Edition), 2011, p. 1673.
Huang et al. "Marked increases in Resting-State MEG Gamma-Band Activity in Combat-Related Mild Traumatic Brain Injury," Cerebral Cortex, Jan. 2020, pp. 283-295.
Huijbers et al., "Tau Accumulation in Clinically Normal Older Adults is Associated with Hippocampal Hyperactivity," The Journal of Neuroscience, Jan. 16, 2019, 39(3), pp. 548-556.
Notification of Transmittal of the international Search Report and Written Opinion, PCT/US2019/063748, Feb. 20, 2020, 7 pages.
Ives, James, "UCPH research receives prize for research into brain's cleaning system," www.news-medical.net/news/20181108/UCPH-researcher-receives-orize-for-r, Retrieved from the Internet Mar. 17, 2020.
Janiri et al., "Shared Neural Phenotypes for Mood and Anxiety Disorders," JAMA Psychiatry, 2020, 77(2) pp. 172-179.
Lammert et al., "AIM2 inflammasome surveillance of DNA damage shapes neurodevelopment," Nature, vol. 580, Apr. 20, 2020, 22 pages.
Lehmann et al., "Analysis of cerebrovascular dysfunction caused by chronic social defeat in mice," Brain, Behavior, and Immunity, 88, 2020, pp. 735-747.

(Continued)

*Primary Examiner* — Raymond J Henley, III
(74) *Attorney, Agent, or Firm* — Stanek Lemon Crouse & Meeks, PA

(57) ABSTRACT

The present inventive concept defines as "Neuroquiescence" a method for treating neurovascular dysregulation underlying neurodevelopmental and neurodegenerative dysfunctions by improving immunovascular robustness for fueling glial cells while pausing neuronal bioelectrical activity for remyelination and astrocyte resetting cellular homeostasis.

19 Claims, 4 Drawing Sheets

(56) References Cited

OTHER PUBLICATIONS

Lenz et al., "Systemic thrombin inhibition ameliorates seizures in a mouse model of pilocarpine-induced status epilepticus," Journal of Molecular Medicine, Nov. 2019, vol. 97, Issue 11, pp. 1567-1574.
"Longevity Linked to Proteins That Calm Overexcited Neurons," https://www.quantamagazine.org/longevity-linked-to-proteins-that-calm-overexcited-neurons-20191126/, Retrieved from the Internet Mar. 17, 2020.
Ma et al., "Demyelination contributes to depression comorbidity in a rat model of chronic epilepsy via dysregulation of Olig2/LING0-1 and disturbance of calcium homeostatis," Experimental Neurology, 321, 2019, 12 pages.
Manno et al., "New Management Strategies in the Treatment of Status Epilepticus," Mayo Clinic Proceedings, 2003, vol. 78, Issue 4, p. 508.
Milikovsky et al., "Paroxysmal slow cortical activity in Alzheimer's disease and epilepsy is associated with blood-brain barrier dysfunction," Sci. Transl. Med, 11, Dec. 4, 2019. 11 pages.
"Neurons energy organelle protected from damage linked to ALS & Alzheimer's", https://neurosciencenews.com/mitochondria-als-alzheimers-15457/, Retrieved from the Internet Mar. 17, 2020.
Ouellette et al., "Vascular contributions to 16p11.2 deletion autism syndrome modeled in mice," Nature Neuroscience, Jul. 13, 2020, 33 pages.
Phan et al. "A myelin-related transcriptomic profile is shared by Pitt-Hopkins syndrome models and human autism spectrum disorder," Nature Neuroscience, vol. 23, Mar. 2020, 31 pages.
Rice et al., "Function and Mechanism of Myelin Regulation in Alcohol Abuse and Alcoholism," BioEssays, 41, 2019, 9 pages.
Schallmo et al. "Weaker neural suppression in autism." Nature Communications, 11, 2020, 13 pages.
Schnier et al., "Nation-wide retrospective, data-linkage, cohort study of epilepsy and incident dementia," Neurology, 2020, 33 pages.
Scientists solve century-old neuroscience mystery; answers may lead to epilepsy treatment, www.eurekaalert.org/pub-releases/2018-11/vt-ssc110618.php, Retrieved from the Internet Mar. 17, 2020.
Shorvon et al., The treatment of super-refractory status epilepticus: a critical review of available therapies and a clinical treatment protocol. Brain, 2011, pp. 1-17.
Sierra et al., "Neuronal Hyperactivity Accelerates Depletion of Neural Stem Cells and Impairs Hippocampal Neurogenesis," Cell, 16, 2015, pp. 488-503.
Tobinick, Edward, "Perispinal etanercept: a new therapeutic paradigm in neurology," Expert Rev. Neurother., 10(6), 2010, pp. 985-1002.
Tobinick et al., "Rapid cognitive improvement in Alzheimer's disease following perispinal etanercept administration," Journal of Neuroinflammation, 5(2), Jan. 9, 2008, 10 pages.
Vadodaria et al., "Serotonin-induced hyperactivity in SSRI-resistant major depressive disorder patient-derived neurons," Molecular Psychiatry, 24, 2019, pp. 795-807.
"Vascular development may be at risk in autism," Ottawa Hospital Research Institute, Jul. 13, 2020, 3 pages.
Verdugo et al., "Glia-neuron interactions underlie state transitions to generalized seizures," Nature Communications, 10, 2019, 13 pages.
Yin et al., "Chemical Conversion of Human Fetal Astrocytes into Neurons through Modulation of Multiple Signaling Pathways," Stem Cell Reports, vol. 12, Mar. 5, 2019, pp. 488-501.
Yuan et al., "Attenuation of β-Amyloid Deposition and Neurotoxicity by Cherriogenetic Modulation of Neural Activity," The Journal of Neuroscience, 36, Jan. 13, 2016, pp. 632-641.
Zullo et al., "Regulation of lifespan by neural excitation and REST," Nature, vol. 574, Oct. 17, 2019, 24 pages.
Kurita et al., "Dobutamine, a β1 Adrenoceptor Agonist, Increases Cerebral Oxygenation During Acute Anemia and Apneic Hypoxia." Neurocrit Care 2017, 27, p. 420-429.
*Non-official translation* "Epileptic status in children, instructions guidelines N30, Moscow City Government, Department of Health Care Services of Moscow," Moscow, 2013, p. 21-24.
Notification of Transmittal of the International Search Report and the Written Opinion of the International Searching Authority, or the Declaration, PCT/US2021/030561, Aug. 26, 2021, 8 pages.
Hu et al., "Continuous Midazolam Infusion in the Treatment of Uncontrollable Neonatal Seizures," Acta Paediatrica Taiwanica, vol. 44, No. 5, Oct. 30, 2003, pp. 279-281.
Extended European Search Report, EP 19889009.7, Dec. 21, 2021, 8 pages.

* cited by examiner

After administration of Midazolam
2.0 mg/kg

NEUROQUIESCENCE—A TREATMENT FOR NEURODEVELOPMENTAL AND NEURODEGENERATIVE BIOELECTRICAL DYSREGULATION AND DEMYELINATION

CROSS-REFERENCE TO RELATED APPLICATIONS

This application is a continuation-in-part application of U.S. patent application Ser. No. 16/698,444, allowed, filed Nov. 27, 2019, which claims the benefit of U.S. Provisional Patent Application Ser. No. 62/772,811, filed Nov. 29, 2018. This application also is a continuation-in-part application of PCT Application No. PCT/US2019/063748, filed Nov. 27, 2019, and claims the benefit of U.S. Provisional Application Ser. No. 63/019,714, filed May 4, 2020, the entirety of each of which is incorporated herein by reference.

FIELD

The present inventive concept defines as "Neuroquiescence" a method for treating neurovascular dysregulation underlying neurodevelopmental and neurodegenerative dysfunctions including Epilepsy, Seizures, Infantile Spasms, Tremors, Parkinson's, Fibromyalgia, Multiple Sclerosis, Migraine Headache, Dementia, Alzheimer's, Attention Deficit Hyperactivity Disorder, Chronic Anxiety, Autism, Depression, Post-Traumatic Distress Disorder, Chemical Addiction, Impulsivity, Schizophrenia, Bipolar Disorder, Obsessive-Compulsive Disorder, Auditory Agnosia, Auditory Neuropathy, Tinnitus, Stuttering of Speech, Speech Tics, Tourette's, Motor Disorder Tics, and Myalgic Encephalomyelitis (Chronic Fatigue Syndrome).

BACKGROUND

Neurodevelopmental and neurodegenerative dysfunctions include seizures of epilepsy, and seizures of vascular dementia, seizures of febrile illness and other sources of neuroinflammation, seizures of traumatic brain injuries, and seizures of post-neurosurgical seizures.

Neurobiological studies on neuronal noise and agitated neurons in the neurovascular coupling mechanisms expose part of the intersystem dependencies associated with vascular roots of neurological dysfunction. For example:

"Neuronal and glial regulation of CNS angiogenesis and barriergenesis" by Saptarshi Biswas, Azzurra Cottarelli, Dritan Agalliu;

"Nutrition-Responsive Glia Control Exit of Neural Stem Cells from Quiescence" James M. Chell and Andrea H. Brand;

"Regulation of lifespan by neural excitation and REST" by Joseph M. Zullo, Derek Drake, Liviu Aron, Patrick O'Hern, Sameer C. Dhamne, Noah Davidsohn, Chai-An Mao, William H. Klein, Alexander Rotenberg, David A. Bennett, George M. Church, Monica P. Colaiácovo, and Bruce A. Yankner;

"Neuronal Hyperactivity Accelerates Depletion of Neural Stem Cells and Impairs Hippocampal Neurogenesis" by Amanda Sierra, Soraya Martín-Suárez, Roberto Valcárcel-Martín, Jesús Pascual-Brazo, Sarah-Ann Aelvoet, Oihane Abiega, Juan J. Deudero, Amy L. Brewster, Irantzu Bernales, Anne E. Anderson, Veerle Baekelandt, Mirjana Maletić-Savatić, Juan M. Encinas;

"Reduction of hippocampal hyperactivity improves cognition in amnestic mild cognitive impairment" by Arnold Bakker, Gregory L. Krauss, Marilyn S. Albert, Caroline L. Speck, Lauren R. Jones, Craig E. Stark, Michael A. Yassa, Susan S. Bassett, Amy L. Shelton, and Michela Gallagher;

"Tau Accumulation in Clinically Normal Older Adults Is Associated with Hippocampal Hyperactivity" by Willem Huijbers, Aaron P. Schultz, Kathryn V. Papp, Molly R. LaPoint, Bernard Hanseeuw, Jasmeer P. Chhatwal, Trey Hedden, Keith A. Johnson, and Reisa A. Sperling;

"Attenuation of β-Amyloid Deposition and Neurotoxicity by Chemogenetic Modulation of Neural Activity" by Peng Yuan, and Jaime Grutzendler;

"Role of Microglial Cells in Alzheimer's Disease Tau Propagation" Ena Španić, Lea Langer Horvat, Patrick R. Hof and Goran Šimić;

"Convergence and divergence in the etiology of myelin impairment in psychiatric disorders and drug addiction" by Yue Feng;

"Function and Mechanism of Myelin Regulation in Alcohol Abuse and Alcoholism" by James Rice, Chen Gu;

"Shared Neural Phenotypes for Mood and Anxiety Disorders: A Meta-analysis of 226 Task-Related Functional Imaging Studies" by Sophia Frangou, University of British Columbia;

"Serotonin-induced hyperactivity in SSRI-resistant major depressive disorder patient-derived neurons" by Krishna C. Vadodaria" Salk Institute;

"AIM2 inflammasome surveillance of DNA damage shapes neurodevelopment" Lammert, Elizabeth L. Frost, Calli E. Bellinger, Ashley C. Bolte, Celia A. McKee, Mariah E. Hurt, Matt J. Paysour, Hannah E. Ennerfelt, and Lukens;

"Weaker neural suppression in autism" by Michael-Paul Schallmo, Tamar Kolodny, Alexander M. Kale, Rachel Millin, Anastasia V. Flevaris, Richard A. E. Edden, Jennifer Gerdts, Raphael A. Bernier, Scott O. Murray;

Study Finds High Levels of Abnormally Fast Brain Waves in Mild Brain Injury by Mingxiong Huang—Department of Veterans Affairs (VA) and the Navy;

Possible Culprit of Fibromyalgia Found: Microglial Activation "Brain glial activation in fibromyalgia—A multi-site positron emission tomography investigation" by Albrecht, D. S., Forsberg, A., Sandström, A., Bergan, C., Kadetoff, D., Protsenko, E., and Loggia, M. L;

"Glia-neuron interactions underlie state transitions to generalized seizures" by Carmen Diaz Verdugo, Sverre Myren-Svelstad, Ecem Aydin, Evelien Van Hoeymissen, Celine Deneubourg, Silke Vanderhaeghe, Julie Vancraeynest, Robbrecht Pelgrims, Mehmet Ilyas Cosacak, Akira Muto, Caghan Kizil, Koichi Kawakami, Nathalie Jurisch-Yaksi & Emre Yaksi;

"Demyelination contributes to depression comorbidity in a rat model of chronic epilepsy via dysregulation of Olig2/LINGO-1 and disturbance of calcium homeostasis" by Teng Ma, Baichuan Li, Yifan Le, Yang Xu, Fei Wang, Yanping Tian, Qiyan Cai, Zhi Liu, Lan Xiao, Hongli Li;

Drugs that quell brain inflammation reverse dementia Electroencephalograms (EEGs) revealed similar brain wave disruption, or paroxysmal slow wave events, in humans with epilepsy and with cognitive dysfunction, including Alzheimer's and mild cognitive impairment (MCI) by Alon Friedman and Daniela Kaufer;

Inadequate Myelination of Neurons Tied to Autism: Study "A myelin-related transcriptomic profile is shared by Pitt-Hopkins syndrome models and human autism spectrum disorder" by BaDoi N. Phan, Joseph F. Bohlen, Brittany A. Davis, Zengyou Ye, Huei-Ying Chen, Brent Mayfield, Srinidhi Rao Sripathy, Stephanie Cerceo Page, Morganne N. Campbell, Hannah L. Smith, Danisha Gallop, Hyojin Kim, Courtney L. Thaxton, Jeremy M. Simon, Emily E. Burke, Joo Heon Shin, Andrew J. Kennedy, J. David Sweatt, Benjamin D. Philpot, Andrew E. Jaffe, Brady J. Maher;

"Nation-wide retrospective, data-linkage, cohort study of epilepsy and incident dementia" New findings show patients with epilepsy had a 3.1 times higher hazard of incident vascular dementia, a 2.5 times higher hazard of incident dementia, and a 1.6 times higher hazard of Alzheimer's disease by Christian Schnier, Susan Duncan, Tim Wilkinson, Gashirai K Mbizvo, and Richard F. M. Chin;

"The heart-brain connection: The link between Long QT Syndrome and seizures" by David Auerbach; and "Psychological Stress Damages Brain's Blood Vessels," Mouse Study Illuminates Potential Mechanism Behind Mood and Anxiety Disorders, "Analysis of cerebrovascular dysfunction caused by chronic social defeat in mice" by Michael L Lehmann, Chelsie N Poffenberger, Abdel G Elkahloun, Miles Herkenham. The contents of these studies are incorporated herein by reference as if set forth in their entirety.

Further, an article published Jul. 13, 2020 in "Nature Neuroscience" entitled "Vascular contributions to 16p11.2 deletion autism syndrome modeled in mice" by Dr. Baptiste Lacoste and colleagues detail vascular contributions to 16p11.2 deletion autism syndrome modeled in mice. The contents of this study are incorporated by reference as if set forth in its entirety.

Dr. Baptiste Lacoste, a scientist at The Ottawa Hospital and an assistant professor in the University of Ottawa's Faculty of Medicine and Brain and Mind Research Institute, heads a lab that specializes in neurovascular interactions in health and disease. In collaboration with researchers at McGill University, Laval University, and the National Research Council of Canada, Dr. Lacoste's team used a mouse model with one of the most common genetic mutations found in autism spectrum disorder—16p11.2 deletion.

"A Canadian collaboration led by Dr. Baptiste Lacoste has undertaken the first ever in-depth study of vasculature in the autistic brain. The product of four years of work, a paper published today in Nature Neuroscience lays out several lines of novel evidence that strongly implicate defects in endothelial cells—the lining of blood vessels—in autism." Released by the University of Ottawa Faculty of Medicine, Jul. 13, 2020.

Currently, there remains a need for improved methods and protocols for resolving disorders related to bioelectrical dysregulation in neurons, such as epilepsy, and seizures associated with epilepsy and other neurological dysfunctions.

SUMMARY

As demonstrated with Epilepsy, aspects of the inventive concept resolve the root-cause of neuronal agitation by mitigating the vascular impediments to robust bloodflow to microvessels for oxygenation of neurons and glial cells, and then with bioelectrical pause of neuronal activity, avails glial cells accelerated remyelination.

The inventive concept has been demonstrated in humans to enable the brain to fully resolve even "intractable" Epilepsy and has two important contributors to success.

The first contributor is fueling glial cells via robust bloodflow for nutrients and oxygenation. Mitigating the environment of deficient bloodflow to microvessels is imperative for disrupting the neurovascular sequence of causes and effects.

The second contributor to the success of our protocol is using anesthesia to pause bioelectrical activity of neurons.

This bioelectrical pause enables neuronal repairs that cannot happen during bioelectrical activity. The bioelectrical pause also removes the capacity loading of neurons from the localized bloodflow resources so that glial cells are availed maximum fuel for neuronal repairs.

Neuroquiescence demonstrates that glial capacities are limited only by bloodflow and oxygenation availed to fuel them. Bioelectrical pause not only allows neuronal repairs and remyelination, it enables fueling those neuronal repairs at an accelerated rate. Preparations for maximizing this fueling of glial cells requires robust bloodflow which takes weeks of preparation to accomplish.

Furthermore, one of the challenges with brain surgeries is the risk of developing seizures even if there were none before. Epilepsy surgeries risk failing the patient to become seizure-free by a similar percentage as those who develop seizures from neurosurgeries of other purposes. Neuroquiescence has a special section for post-surgical seizure risk management and mitigation.

Common methods of stimulating bloodflow include the noninvasive "Transcranial Magnetic Stimulation" and the implanted electrode surgery "Deep Brain Stimulation". These strive to assist patients with Epilepsy, Parkinson's and other neuromuscular disorders, Narcolepsy, Depression, Obsessive Compulsive Disorders, Tourette's, Addictions . . . . For those with Epilepsy, "Deep Brain Stimulation" strives to manage seizures, but the neuronal agitation would rarely end.

Neuroquiescence has been demonstrated to fully resolve the neuronal agitation associated with Epilepsy, and is expected to fully resolve the other dysfunctions for which "Deep Brain Stimulation" is attempted.

Accordingly, in some aspects of the inventive concept, Dobutamine is used as a medication for vasodilation and fueling glial cells via robust bloodflow for nutrients and oxygenation.

In adults and children, Dobutamine surpassed the usefulness of any "antiseizure" medication because Dobutamine addresses the root-cause of agitated neurons, the deficiency in oxygenation via bloodflow.

Dobutamine alone is not a replacement for Neuroquiescence but its functionality of stimulating robust bloodflow is imperative for Neuroquiescence. All manifestations of neurological dysfunctions for which Neuroquiescence is expected to be beneficial have agitated neurons and demyelination. The first step as a treatment for all these manifestations of neurological dysfunctions is to improve bloodflow. The best way we know right now, well proven for Epilepsy, is Dobutamine.

There are several intersystem effects involved. One of these is demonstrated in studies on the blood-brain barrier breakdown, circulating proteins that trigger neuroinflammation, a pattern repeated in Epilepsy, Alzheimer's, Autism, and other diseases associated with demyelination. Evidence supports neurovascular sequence of dysfunctional causes and effects in that the blood-brain barrier is being repaired when bloodflow is robust enough to support the glial cells, astrocytes, and interneurons through vasoactive feedback to repair vasodilation and vasoconstriction responses.

Because the effects of our Neuroquiescence protocol have been so repeatable and sustained in resolving Epilepsy, verified in fMRI with improving trajectories in brain health, and because one of the effects of Epilepsy is demyelination, evidence implies that remyelination is occurring.

Evidence from neurobiological studies on segments within the neurovascular sequence of dysfunctional causes and effects indicate likely success that all neurological dysfunctions that include neuronal agitation or demyelination can be disrupted by our protocol Neuroquiescence. Bioelectrical pause by sedation in the presence of robust bloodflow fuels glial cells for neurological repairs. However, sedation during deficiencies in bloodflow bring neurological risks.

Lessons learned from Neuroquiescence suggest that sustained sedation or even a coma should include monitoring blood viscosity and ensuring robust bloodflow to avoid entering the neurovascular sequence of dysfunctional causes and effects.

Genetic correlations require specific environmental conditions to manifest as a specific neurological dysfunction. Maladaptations attributed to genetics are rarely 100% indicators independent of environmental conditions. Babies who have genetics correlated with Epilepsy but who had robust oxygenation into childhood never had the environmental conditions for those genetic risks to manifest.

The present inventive concept is related to resolving and healing bioelectrical dysregulation of neurons that induce seizures associated with, for example, epilepsy. "Neuroquiescence," is the process of using sustained sedation to enable glial biomechanisms maximum capacity for neuronal healing, remyelination, pruning, and disconnections of maladapted circuits formed due to agitated neurons. Neuroquiescence as described herein is safe because it was designed for babies, and has been used for neonates, infants, toddlers, children, and teenagers, for whom over 95% of cases resolved of all symptoms of Epilepsy, including the neurophysiological root-cause, thereby enabling a trajectory away from any risk of any return of bioelectrically agitated neurons.

According to an aspect of the inventive concept, provided is a method for enabling the glial cells to heal the neuronal maladaptations and the demyelinating effects of seizures associated with an epileptic disorder in a subject in need thereof comprising: preparing cerebrovascular robustness of bloodflow and oxygenation, and then medically sedating the subject for a sustained period of time by administering a therapeutically effective amount of an anesthetic, wherein the sedating of the subject pauses bioelectrical activity of neurons in the subject to facilitate healing of the neurons in the subject.

According to another aspect of the inventive concept, provided is a method for treating irregular, abnormal, or excessive neuronal activity associated with an epileptic disorder in a subject in need thereof comprising: medically sedating the subject for a sustained period of time by administering a therapeutically effective amount of an anesthetic, wherein the sedating of the subject pauses bioelectrical activity of neurons in the subject to facilitate healing of the neurons in the subject.

According to yet another aspect of the inventive concept, provided is a method for pausing bioelectrical activity in neurons in a subject suffering from an epileptic disorder comprising: medically sedating the subject for a sustained period of time by administering a therapeutically effective amount of an anesthetic, wherein the pausing of bioelectrical activity facilitates healing of neurons exhibiting irregular, abnormal, and/or excessive activity.

According to another aspect of the inventive concept, provided is a method for reducing neuronal agitation and cellular oxygenation deficiencies in a subject in need thereof comprising administering a therapeutic amount of Dobutamine to improve microvasculature transport of bloodflow.

According to yet another aspect of the inventive concept, provided is a method for enabling remyelination and neurological repairs in a subject in need thereof comprising medically sedating the subject for a minimum of three days by administering a therapeutically effective amount of an anesthetic for pausing bioelectrical activity of neurons for systemic repairs

DETAILED DESCRIPTION

Figure 1:
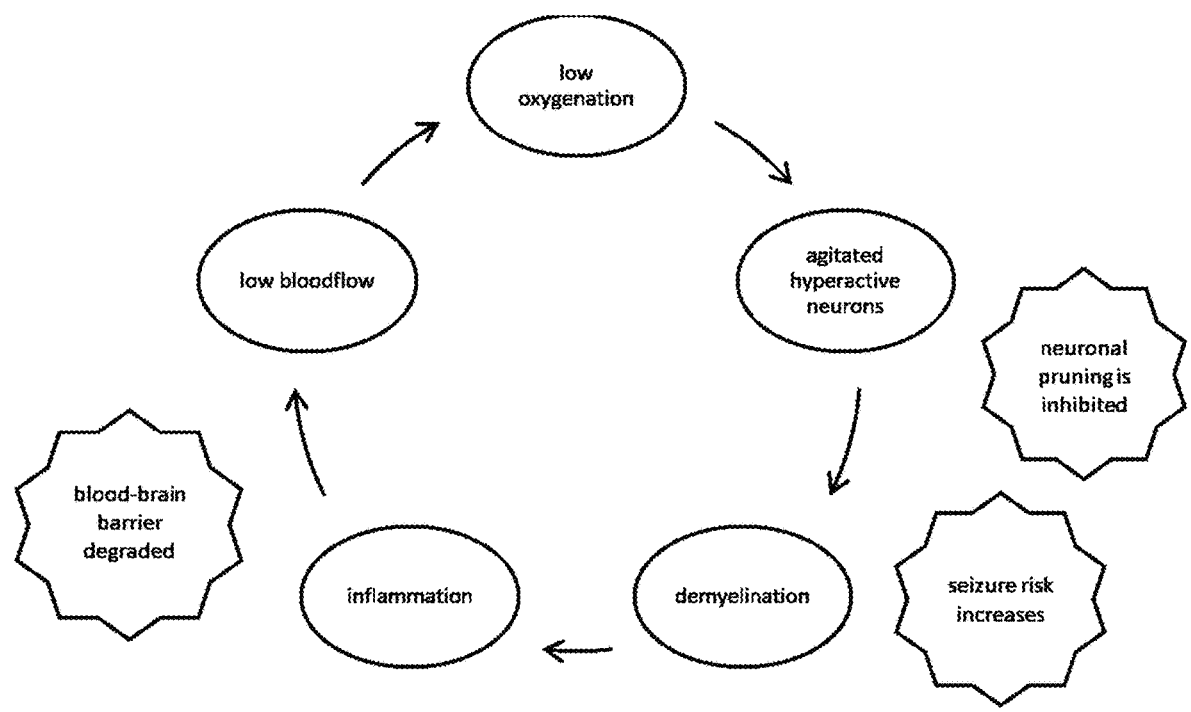
FIG. 1 depicts the loop of dysfunctional causes and effects of neurovascular events in disorders involving neurological and nervous system bioelectrical dysregulation.

In the following detailed description, embodiments of the present inventive concept are described in detail to enable practice of the inventive concept. Although the inventive concept is described with reference to these specific embodiments, it should be appreciated that the inventive concept can be embodied in different forms and should not be construed as limited to the embodiments set forth herein. Rather, these embodiments are provided so that this disclosure will be thorough and complete, and will fully convey the scope of the inventive concept to those skilled in the art. All publications cited herein are incorporated by reference in their entireties for their teachings.

The inventive concept includes numerous alternatives, modifications, and equivalents as will become apparent from consideration of the following detailed description.

Unless otherwise defined, all technical terms used herein have the same meaning as commonly understood by one of ordinary skill in the art to which this disclosure belongs.

Also as used herein, the terms "treat," "treating" or "treatment" may refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

As used herein, the terms "prevent," "preventing" or "prevention of" (and grammatical variations thereof) may refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the inventive concept. In representative embodiments, the term "prevent," "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present inventive concept.

An "effective amount" or "therapeutically effective amount" may refer to an amount of a compound or composition of this inventive concept that is sufficient to produce a desired effect, which can be a therapeutic and/or beneficial effect. The effective amount will vary with the age, general condition of the subject, the severity of the condition being treated, the particular agent administered, during the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, The Science and Practice of Pharmacy (latest edition)).

The need for Neuroquiescence

Neuroquiescence is a procedure, a protocol used by specialized neurologists, anesthesiologists and radiologists; there are no new medications required as we use only existing FDA-approved medications and equipment.

Neuroquiescence improves cerebrovascular bloodflow to a robust level, and then pausing the affected neurons' bioelectrical activity for glial cell repairs. As initially envisioned, this protocol would mitigate the root-cause and run the pathogenesis of Epilepsy in reverse. The development of Neuroquiescence is rooted in the following conceptualization of the pathogenesis of Epilepsy:

Cerebral electrical activity (whether bioelectrical or artificial) stimulates bloodflow.

Deficiencies in microvascular bloodflow agitate neurons for bioelectrical signaling to stimulate vascular support for transport of oxygen; this neuronal agitation serves a purpose for their survival.

If the neuron's expending bioelectrical energy for more oxygenation through bloodflow succeeds, the neuron becomes stable.

If the neuron's expending bioelectrical energy for more oxygenation through bloodflow is not successful, the bioelectrical agitation may stimulate even well-oxygenated neurons toward dysfunctional interconnections without appropriate inhibitory and excitatory links.

Bioelectrically-saturated neurons can become locked into a dysregulated feedback-loop that expends all the neuron's energy capacity while also disabling pruning and glial assistance in remyelinating. Bioelectrical pulsing synchronizes within the interconnected cluster of neurons, thereby increasing the amplitude of the neuroelectromagnetic field measured on EEG, and further exhausting the energy available in bloodflow and glial support.

Even a low quantity of neurons agitated by low bloodflow and deficient oxygenation may interconnect into dysfunctional circuits of synchronized neuronal activity, thereby exhausting the local bloodflow supply of oxygen, stressing vascular capacity, leaving otherwise healthy neurons in an oxygenation deficit.

A circular feedback-loop of maladaptively interconnected neurons may be susceptible to oscillation even after the microvessels and cerebrovascular bloodflow have improved.

When later observed, vascular health in this region of neuronal agitation may appear nominal because it had time to improve in response to the agitated bioelectrical activity. Still, there may be deficient bloodflow and oxygenation for the neurons to disconnect from their maladaptive interconnections and heal, even when we pause their bioelectrical activity. We therefore improve their microvascular environment.

Evidence that the pathogenesis of Epilepsy is about cerebrovascular connectivity to microvessels for oxygenation of neurons by robust bloodflow is made apparent in the difference between the first-week sedation to ease the removal of antiseizure medications versus the sixth-week results of sedation after the cerebrovascular bloodflow is made more robust.

In week one with a patient, all antiseizure medications are removed and an initial sedation session of six days is only for easing this transition of their nausea and their constant seasickness feeling.

Even after week-one of Dobutamine and a six-day initial sedation, 10% to 15% of our children were resolved of not only their seizures, but their neuronal agitation noise as well never returned.

Weeks two through five are our Pre-Neuroquiescence preparations of cerebrovascular bloodflow and oxygenation, and there is typically no sedation and never any antiseizure medication. For those at risk of seizures, the initial sedation session was extended through week six so that the Dobutamine had time to avail better bloodflow for those agitated neurons. For about 80% of our children, although there were no seizures, the neuronal agitation noise was still present.

In week-six (or a few weeks later if cerebrovascular bloodflow is not yet robust) the patient was subjected to the Neuroquiescence sedation session, resulting in over 95% of our children having no neuronal agitation noise, and it never returns; their brains continue becoming healthier as we continue the Dobutamine, the EEG monitoring, and the fMRI monitoring are continued as part of a post-sedation period.

The only difference between week-one and week-six is the duration of time our children had on Dobutamine for producing a robust cerebral bloodflow. Robust oxygenation with robust cerebral bloodflow are indicated in the comparison between week-one versus week-six as fundamental to the root-cause of Epilepsy, and therefore fundamental to the environment supporting the self-mitigation of neuronal maladaptations.

The objective of this treatment is to enable glial cells to assist agitated and hyperactive neurons to remyelinate and reset to cellular homeostasis. While glial cells persistently strive to accomplish this in normal neuronal function, glial cells cannot keep up during a neuronal dysregulated state of saturated bioelectrical activity, so remyelinating and perhaps pruning cannot occur. Achieving healing of agitated neurons requires that their bioelectrical activity be paused.

Cerebrovascular resilience supports oxygenation of neurons. Deficiencies in cerebral bloodflow or microvascular support of neurons increases their agitated activity. Neuronal agitation activity exhausts oxygen levels which are already low, and surrounding neurons become agitated. Febrile illness or strenuous exercise when in a constricted bloodflow state can induce exhaustion of oxygen levels at the neurons thereby stimulating neuronal agitation. Inconsistent microvascular transport of oxygen increases inflammation around the neurons thereby inhibiting healing.

Immunoinflammatory imbalance associated with diminished oxygenation during sleep is a threat to neuronal health. Oxygen transfer deficiencies in lungs to vascular transport and into microvascular support of neurons decreases during sleep thereby increasing risks of seizures. During sleep, autoregulation reduces bloodflow which increases risk of low oxygenation to neurons which may be above the threshold needed to avoid agitation during the day. Sleep issues such as restless leg syndrome may be indicative of deficiencies in oxygenation to the sensory neurons in the legs, and over time these neurons may become hyperactive and produce sustained itchiness or other symptoms.

Those with a chronic asthma or bronchitis are more susceptible to risk of neuropathic pain later in life due to deficiencies in oxygenation for sensory neurons, and as children are more likely to have issues such as stuttering of speech or auditory agnosia due to decreased oxygenation in regions of the brain.

Genetic factors increase neurophysiological distinctions that expose susceptibility to "mitochondrial Epilepsy" induced by cerebral vasospasm or pulmonary vasospasm and factors influencing bloodflow and oxygen-transfer efficiencies. These genetic factors can be overwhelmed by our changing the environment before neuronal bioelectrical activity becomes disruptive by preemptively applying vasodilation and oxygenation functions of our protocol. We can also pause neuronal bioelectrical activity to allow healing of the maladapted cells if preemptive intervention was too late.

In some embodiments, the subject may be medically sedated deeply enough to pause bioelectrical activity for a continuous and sustained period of a minimum of three days for enabling glial cells their neuronal repairs and remyelination.

Pausing of bioelectrical activity of neurons as will be appreciated by anesthesiologists skilled in the art may be defined as the reduction of amplitude and/or frequency of bioelectrical waveforms associated with quieting the electrical activity of neurons during sedation. The pausing of bioelectrical activity may be monitored, for example, by an electroencephalogram (EEG). The bioelectrical waveforms that are paused according to embodiments of the present inventive concept may be abnormal bioelectrical waveforms associated with neurological disorders, such as epilepsy.

Glial remyelination and resolving neuronal maladaptive connections according to embodiments of the present inventive concept will be appreciated by one of skill in the art, may be defined as the restoration of normal function of neurons that exhibit irregular, abnormal, and/or excessive bioelectrical activity, such as may be manifested as part of a neurological disorder, such as epilepsy.

It will be appreciated that monitoring of bioelectrical activity of neurons during medical sedation for a sustained period of time may be performed to assess the extent of healing of neurons in a subject, and the period of time for medical sedation may be adjusted depending upon the extent of healing which takes place during medical sedation.

Embodiments of the present inventive concept include: Vasodilation as Prophylaxis for Infantile Spasms and Epilepsy; Neuroquiescence for Epilepsy in Children; and Neuroquiescence for Epilepsy in Adults.

Medications

The Neuroquiescence Protocol defines functions of medications and not specific medications, although the medications listed are the ones we have used, it is by no means intended to be limited thereto. All medications used according to the present inventive concept are selected based upon their approved function; immunoinflammatory medications or oxygenation medications or anesthesia medications are so chosen for their known and approved functions.

Exemplary medication schedules of a Neuroquiescence protocol are set forth as follows. An overview of an exemplary protocol including: week one of sustained sedation and removal of antiseizure medications; a number of weeks (weeks two through five, for example, in children, longer in adults) as part of a preparation period with vasodilation and oxygenation and with no sedation and no antiseizure medication; a second Neuroquiescence/sedation session at week six (later for adults, for example nine weeks); and a post-sedation period with medications for vasodilation and oxygenation are outlined in Table I. Use of Midazolam (anesthesia) for an exemplary six-day extended Neuroquiescence/sedation session is outlined in Table II. Prior to a Neuroquiescence Protocol and/or during the first week of the protocol, the patient should be removed from any of the existing anti-seizure medication, such as Tegretol, Tegretol XR, Carbatol, Equetro, Teril, Diazepam, Phenytoin, Carbamazepine, Valproic Acid, Ethosuximide, etc.

Vasodilation Function: a medication-induced improvement in vascular capacity and throughput of bloodflow Vasodilation has proven to be an element in resolving agitated neurons, better improving bloodflow and oxygenation. We have two sedation periods, week-one and week-six. Only about 20% of cases come out of week-one with no return of neuronal agitation, but after the vasodilation medication has an opportunity to work, 95% come out of the sixth week Neuroquiescence session with no return of the neuronal agitation.

Brainscans for evaluation of Cerebral Bloodflow (CBF) and Intracranial Pressure (ICP) are required for determining which of two vasodilation medications fit the need.

Dobutamine: when the spatial area of impeded bloodflow is larger; this also used as an ongoing maintenance vascular dilation medication.

Prostin: for neonates with small spatial area of impeded bloodflow; Prostin also may be useful for older patients where bloodflow is good but oxygenation is still deficient. Prostin is not used in ongoing maintenance because of the need for persistent monitoring for risk of cerebral-bleeding and/or congestive heart failure and/or hypertension.

Oxygenation Function: a medication-induced improvement in the oxygen transfer functions and transport levels in the blood The oxygen transfer efficiency of the entire respiratory system must be confirmed, from the secure airway, through blood-oxygen levels, through appropriate brain oxygenation.

A supplemental oxygen pediatric nasal mask is recommended during sedation for Neuroquiescence, thereby providing a more comfortable fit and improved respiratory support yielding oxygenation saturation of 90% to 94%.

Especially for children diagnosed with chronic Asthma or Bronchitis and cases wherein oxygenation is most challenged, we have combined the IV-based oxygenation medication with the oxygen mask, and only under close medical supervision monitoring blood-oxygen levels.

Nasal Mask:

Ipratropium (inhalation)

Respiratory anticholinergic—Ipratropium, Tiotropium or Aclidinium

Short duration: Beta-2 Agonist; bronchial relaxant (not to exceed 30 mcg per day). Albuterol, and Levalbuterol.

Long duration oral or IV: increased selectivity in neuroreceptors; long acting Beta-2 Agonist; relaxes bronchial smooth muscle by acting selectively on Beta-2 receptors; heartrate may be slowed. Salmeterol, Formoterol, Arformoterol, Vilanterol, Indacaterol, and Xanthine's (derivatives).

Counterinflammation Function: a medication-induced reduction of inflammatory impediments to oxygenation and healing of neurons Anti-inflammatory medications Cyclophosphamide and Ketoprofen are used in alternating weeks. Cyclophosphamide; IV or PO (oral); daily 8 to 20 mg per kg, and Ketoprofen; IV or PO (oral); 75 mg per kg PO over q8 hr or 50 mg per kg PO q6 hr Neuroquiescence Function: a medication-induced sedation sustained to pause bioelectrical activity of neurons for their healing Note: This procedure shall never be used except under the guidance of an anesthesiologist with EEG monitoring plus and all standard critical functions monitoring.

Midazolam IV dosage at 0.2 mg/kg (Maximum 10 mg) is effective in termination of frequency of seizure and Grand mal seizure associated with loss of consciousness and other neuropathology. Midazolam is well absorbed when administered by IV, but it is necessary to be prepared to assist with ventilations especially if the patient has a history of brain trauma.

An allergy test is required before the Neuroquiescence session, and we find that approximately 5% are allergic to Midazolam. Neuroquiescence Protocol therefore uses Fentanyl dosage 2-3 mcg/kg IV as an optional sedation medication in case of the patient present positive test result for allergic reaction to Midazolam. Fentanyl compounds are safe and can reduce complications associated with allergic site.

Midazolam Sedation—Pediatric

Refer to Table II. for use of intravenous IV-delivered Midazolam for the Neuroquiescence session. There are six days listed with an initial dose each day followed by the hourly dose listed by bodyweight. The objective is to safely keep the patient deeply sedated enough to pause neuronal bioelectrical activity. If the maximum dose of 5 mcg/kg/min does not achieve control, General Anesthesia with Thiopentone will be required. Pulse Oximetry is mandatory. Establishing the infusion rate of between one and five micrograms per kilogram per minute is a dynamic process with monitoring the EEG for neuronal bioelectrical agitation activity.

Cautions

Macrolides (Erythromycin, Clarithromycin)—inhibit metabolism of Midazolam, and cause excess sedation to occur Phenytoin—Midazolam may make levels unpredictable (decrease or increase phenytoin levels)

Baclofen—Midazolam is also a muscle relaxant and can cause excessive muscle relaxation with Baclofen IV Fentanyl—Continuous Sedation/Anesthesia In the rare case where a patient is allergic to Midazolam, another anesthetic, for example, Fentanyl, may be used and with which similar results as with Midazolam have been exhibited. It will be appreciated by one of skill in the art that more options for anesthesia are available, especially if a patient is allergic to both Midazolam and Fentanyl, and due to decreasing availability of Fentanyl due to misuse.

Methods to induce Neuroquiescence, according to embodiments of the present inventive concept, may include medically sedating a subject by administering a therapeutically effective amount of an anesthetic, for example, but not limited to, midazolam. The medical sedation may take place continuously, for example, over a period of time of about 1 day, 2 days, 3 days, 4 days, 5 days, 6 days, or 7 days (1 week). Midazolam may be administered daily over the period of time which the medical sedation takes place. In some embodiments, the medical sedation of the Neuroquiescence Protocol may be a deep sedation, or may be a general anesthesia, so long as the sedation is sufficient to pause bioelectrical activity, such as abnormal bioelectrical activity, of neurons in a subject with a disorder associated with neurological bioelectrical dysfunction, such as epilepsy or suffering from seizures associated with epilepsy.

In some embodiments, the disorder associated with neurological bioelectrical dysfunction may be seizures associated with epilepsy, such as epilepsy with generalized tonic-clonic seizures, epilepsy with myoclonic absences, frontal lobe epilepsy, temporal lobe epilepsy, benign rolandic epilepsy (BRE), childhood absence epilepsy (CAE), juvenile myoclonic epilepsy (JME), benign occipital epilepsy, Lennox-Gastaut syndrome (LGS), "genetic" or "mitochondrial" epilepsy, SCN2A encephalopathy, Landau-Kleffner Syndrome, Ohtahara syndrome, Rasmussen's syndrome, West's syndrome, Rett syndrome, CDKL5 disorder, essential tremor, Dravet syndrome, Doose syndrome, acute repetitive seizures, status epilepticus, refractory status epilepticus, super-refractory status epilepticus (SRSE), PCDH19 pediatric epilepsy, increased seizure activity, and breakthrough seizures.

In embodiments of the inventive concept, the subject may be a human subject. Human subjects of any gender (for example, male, female or transgender) and at any stage of development (i.e., neonate, infant, juvenile, adolescent, adult, elderly) diagnosed with, for example, a seizure associated with epilepsy, may be treated according to the methods and protocols of the present inventive concept.

Dosages to medically sedate the subject are not particularly limited, so long as the sedation, and pausing of bioelectrical activity of neurons are maintained by the dosage. In some embodiments, midazolam is administered to the subject at a dosage of about 0.2, 0.3, 0.4, 0.5, or 0.6 mg/kg. Similarly, the rate of administration, for example, intravenous administration, is not particularly limited, so long as the desired effect, e.g., pausing of bioelectrical activity to avail healing, is achieved and/or maintained. In some embodiments, midazolam is administered at a rate of about 0.5, 1.0, 2.0, 3.0, 4.0, or 5.0 mcg/kg/min.

In other embodiments of the present inventive concept, the anesthetic may be administered for a second period at a time after the first or initial period of medical sedation. In some embodiments, the second period of medical sedation takes place about 4, 5, 6, 7, 8, 9, or 10 weeks after the first or initial period of medical sedation. In some embodiments, the second period of medical sedation takes place about 6 weeks after the first or initial period of medical sedation. In some embodiments, the second period of medical sedation takes place about 9 weeks after the first or initial period of medical sedation.

In yet other embodiments, Neuroquiescence may be induced in conjunction with administering of additional medications useful in treating or preventing seizures associated with an epileptic disorder, or treating or preventing irregular, abnormal, or excessive neuronal activity. For example, Neuroquiescence may be induced in conjunction with a therapeutically effective amount of a medication to induce vasodilation, oxygenation, and/or to reduce inflammation before, during, and/or after medical sedation of the subject. The medication to induce vasodilation, oxygenation, and/or to reduce inflammation is not particularly limited, and may be any that would be appreciated by one of skill in the art.

Neuroquiescence may be followed, in some embodiments, by monitoring of bioelectrical activity of neurons by monitoring bioelectrical activity, for example, on an electroencephalogram (EEG), and/or with functional magnetic resonance imaging (fMRI), or by any method of monitoring bioelectrical activity of neurons as would be appreciated by one of skill in the art.

In still other embodiments of the present inventive concept, Neuroquiescence may be induced in conjunction with administration of a therapeutically effective amount of a medication that can induce vasodilation, oxygenation, and/or reduction of inflammation. The medication may by administered prior to, during, and/or after a medical sedation/Neuroquiescence session. The medication that is administered and the route of administration of the medication to induce vasodilation, oxygenation, and/or reduction of inflammation is not particularly limited, and may be any that would be envisioned by one of skill in the art.

In some embodiments of the present inventive concept, the use of vasodilation with oxygenation medications would enable even conventional existing antiseizure medications to better do what they do, for example, as a temporary solution until these patients can be engaged with Neuroquiescence, for example, for those patients who are said to be "resistant," i.e., not responsive to conventional existing antiseizure medications.

In other embodiments of the present inventive concept, the use of vasodilation and oxygenation for neonates can disrupt the typical flow of "genetic or mitochondrial epilepsy" seizures or infantile spasms. The use of vasodilation as preemptive care should become standard when brainscans and bloodflow scans or genetic testing indicate the need. In some embodiments, a vasodilation medication may be used to improve bloodflow in the brain as a preemptive treatment or a mitigation of infantile spasms.

In some embodiments of the present inventive concept, the medication to induce vasodilation is Prostin. In some embodiments, the medication to induce vasodilation is Dobutamine.

In other embodiments of the present inventive concept, Neuroquiescence may be used in addition to existing immunoinflammatory medications. In some embodiments, the immunoinflammatory medication may be a tumor necrosis factor (TNF) inhibitor, for example, etanercept (EN-BREL®). In some embodiments, the etanercept is administered perispinally.

In other embodiments, use of a vasodilation medication to improve cerebrovascular bloodflow to microvessels avails transport capacities of medications to bioelectrically agitated neurons. Vascular dilation to improve cerebrovascular bloodflow improves access for any vascular transported medications to neurons and is nearly always required as a preparation for the sedation phase of Neuroquiescence to enable glial cells their neuronal repairs. This applies beyond neurons in the brain to include motor neurons and sensory neurons to include seizures associated with epilepsy, such as, (Benign Rolandic Epilepsy of Childhood, Absence Epilepsy, Juvenile Myoclonic Epilepsy, Benign Occipital Epilepsy, Lennox-Gastaut syndrome, "genetic" or "mitochondrial" epilepsy); nervous system neuropathy such as Neuropathic Pain, Fibromyalgia, Essential Tremors, Blepharospasm, Nystagmus, Tinnitus, Auditory Neuropathy, Phantom-limb Pain, Involuntary Movement or motor neuron dysregulations, Lewy body Dementia, Alzheimer's, and Cluster Headaches; and infantile spasms, such as Auditory Agnosia, Stuttering of Speech, involuntary movements or loss of muscular control, are considered within the scope of the present inventive concept.

Exemplary aspects of the present inventive concept will be further described as follows.

I. Vasodilation as Prophylaxis for Infantile Spasms and Epilepsy

The protocol of the present inventive concept includes prophylaxis to identify and avoid ever having even the first seizure. Exemplary is a toddler who had low bloodflow in the left hemisphere, exhibiting symptoms of Infantile Spasms, and had neuronal agitation which surely would have interconnected enough to cause seizures (see, EXAMPLES, Case Example JH). The chosen medication for vasodilation is Prostin or Dobutamine; after three days the neuronal agitation noise ended; after three months, bloodflow in the left hemisphere was robust; after six months, previous left-hemisphere malformations were approaching normal. We never needed the Neuroquiescence session of sustained sedation as was needed for those who already had progressed to seizures.

We envision in the future where all neonates are checked for robust cerebral hemodynamics and mitigated to overwhelm any genetic risks that would have them on a trajectory toward Epilepsy or Infantile Spasm symptoms from deficient neuronal oxygenation that worsens during sleep.

We advocate using fMRI for inspecting neonatal cerebrovascular bloodflow and mitigating those having less than robust bloodflow and oxygenation. This is especially important for neonates who experienced transient hypoglycemia or transient restriction in oxygenation or bloodflow.

Stuttering of speech is a timing maladaptation due to low cerebrovascular bloodflow between brain regions involved in motor-control required for actuating words, and among the symptoms of Infantile Spasms. Vasodilation and oxygenation improvements may resolve stuttering without requiring a Neuroquiescence session pausing of bioelectrical activity.

II. Neuroquiescence for Epilepsy in Children

The workflow for the Neuroquiescence Protocol will require neurology and anesthesiology expertise. Under no circumstances should anyone without this expertise pursue using the information described here.

All Neuroquiescence Protocol procedures for epilepsy are performed only following analysis of patient seizure activity and nervous system bioelectrical dysregulation. Preliminary work is essentially the same as though we were considering brain surgery, so the reader is presumed to understand this workflow as a starting-point to understanding Neuroquiescence.

Patient Baseline Examination

In embodiments of the present inventive concept, a patient baseline examination may include evaluation of patient: mental status; HEENT (head, ears, eyes, nose, throat); heart; lungs; extremities; neurovascular indication; inflammation; oxygenation graft type-E measurement; seizure rate and quantity, time of day or night, associated activities; antiseizure medications; allergies; trauma; air quality and other environmental exposures; blood-oxygen levels; diabetes and glucose levels and sensitivities or hypoglycemia; loss of consciousness; sleepiness; fever; infantile spam symptoms (bedwetting, stuttered speech, auditory agnosia); tumor; electrolyte abnormality; metabolic or hepatic or renal failure; hypoxia; hyperthermia; blood-pressure hypotension; pediatric assessment triangle (appearance, breathing effort or work of breathing); and brainscans, for example, fMRI, EEG, ECG, oxygenation, and cerebral CT bloodflow scanning.

Neonatal and Special-Needs Children

Special needs children and neonatal diagnostic assessment may require continued use of Pediatric based treatment protocol regardless of age and weight.

Neonatal Seizure

| Etiology | Time Onset |
| --- | --- |
| Hypoxic ischemic encephalopathy | 12-24 hour |
| Drug withdrawal | 24-72 hour |
| Hypocalcemia (nutritional) | 3-7 days |
| Aminoaciduria/organic aciduria | 3-7 days |

The order of the assessment and treatment may require alteration to accommodate the developmental status of the pediatric patient. Neonates, infants and toddlers should never be separated from the caregiver during assessments or when alert during treatments.

The following chart defines week six as the week of meaningful sedation has been the most used approach, but by waiting until the cerebrovascular bloodflow is robust, we optimize the timing of meaningful sedation and reduce likelihood of return of neuronal agitation, and therefore an additional sedation session.

| Week of Robust cerebrovascular bloodflow | Week of Neuro-quiescence | Ending for Dobutamine & counter-inflammatory rotation |
| --- | --- | --- |
| Week four or sooner | Week six | Week twelve |
| Week five | Week seven | Week fourteen |
| Week six | Week nine | Week seventeen |
| Week eight | Week twelve | Week twenty-one |
| Week ten | Week sixteen | Week twenty-six |

Establish an fMRI perspective on cerebrovascular bloodflow from week zero and observe changes with the Dobutamine and the alternating weeks of counterinflammatory/anti-neuroinflammation medications. Document at which week cerebrovascular bloodflow appears robust. Wait the additional weeks designated in the chart for the week of Neuroquiescence sustained sedation. Bloodflow should be stable, not improving because it was noted as robust, and not degrading in robustness.

Sedation sessions longer than six days have been used when neuroinflammation was slow to subside given the medications approved for use with children. If a patient is already sedated in a Neuroquiescence session to prevent seizures, the meaningful week begins only after cerebrovascular bloodflow becomes robust by the extra margin designated in the chart.

While nearly all children were ready and responsive in week-six, teenagers who had unmanageable seizures since they were infants required more time for cerebral bloodflow to become robust. These teenagers (the most challenging cases we could find in our Children's hospital search) would have continued to have seizures even after the Dobutamine began in week-one, so their Neuroquiescence session was extended to be sustained for these weeks.

Separately from using extended Neuroquiescence for avoiding the withdrawal sickness or seizures, six days of sustained sedation appeared to be the point of diminishing returns for neuronal healing. If neuronal agitation later returned, there were other impediments to robust oxygenation of those neurons, such as inflammation. (Lung oxygenation issues and dysregulated pancreas issues were rare examples of impediments to resolving neuronal agitation.) If cerebrovascular bloodflow is not robust, transport to microvessels of even the anesthesia is constricted, so the bioelectrical activity of those neurons may not be paused as required for their repair. First achieving robust cerebral bloodflow therefore increases the likelihood of success with a single (six-day) sedation session.

III. Neuroquiescence for Epilepsy in Adults

Adult Epilepsy differs from Children's Epilepsy in that there may be more neurophysiological trauma and neuroinflammation, perhaps more influence from diabetes or previous surgeries. To enable Neuroquiescence the best potential for success, we must resolve impediments to robust cerebrovascular bloodflow and have stable glucose levels.

A medication we use for neuroinflammation is Neurokinin-2 delivered by IV, and we do not combine this with Dobutamine. We alternate weeks between the Neurokinin-2 (Nk2) versus the Dobutamine Infusion (Dob). We are limited to four doses of Neurokinin 2, so we distribute them among the Dobutamine doses to maximize the Neurokinin-2 counterinflammation. We use no Dobutamine on the day before or after the day of Neurokinin-2.

| Nk2 vs Dob | Day 1 | Day 2 | Day 3 | Day 4 | Day 5 | Day 6 | Day 7 |
| --- | --- | --- | --- | --- | --- | --- | --- |
| Week 1 | Dob | Dob | Dob | Dob | Dob | Dob | none |
| Week 2 | Nk2 | none | Dob | Dob | Dob | Dob | Dob |
| Week 3 | Dob | Dob | Dob | Dob | Dob | Dob | none |
| Week 4 | Nk2 | none | Dob | Dob | Dob | Dob | Dob |
| Week 5 | Dob | Dob | Dob | Dob | Dob | Dob | none |
| Week 6 | Nk2 | none | Dob | Dob | Dob | Dob | Dob |
| Week 7 | Dob | Dob | Dob | Dob | Dob | Dob | none |
| Week 8 | Nk2 | none | Dob | Dob | Dob | Dob | Dob |
| Week 9 | Dob | Dob | Dob | Dob | Dob | Dob | Dob |
| Week 10 | Dob | Dob | Dob | Dob | Dob | Dob | Dob |

The preparation phase for Adult Epilepsy is therefore longer than the preparation phase for Children's Epilepsy. Rather than the typical week for the Neuroquiescence sedation being week six as for children, the meaningful sedation for adults is typically in week nine.

| Week of Robust cerebrovascular bloodflow | Week of Neuro-quiescence | Ending for Dobutamine & counter-inflammatory rotation |
| --- | --- | --- |
| Week six or sooner | Week nine | Week fifteen |
| Week eight | Week eleven | Week nineteen |
| Week ten | Week fourteen | Week twenty-four |
| Week twelve | Week seventeen | Week twenty-nine |
| Week fourteen | Week twenty | Week thirty-four |

Children Epilepsy Protocol Chart

| Function | Medication | Week One | Pre-Neuroquiescence | Neuroquiescence Sedation Session | Post-Neuroquiescence |
|---|---|---|---|---|---|
| Anesthesia Allergy Test | Midazolam preferred | day one | | | |
| Anesthesia Allergy Test | Fentanyl | if allergic to Midazolam | | | |
| Sedation (Anesthesia) (IV) | Midazolam (continuous infusion) | 6 days sustained | | | 6 days sustained |
| Sedation (Anesthesia) (IV) | Fentanyl (continuous infusion) | alternative | | | alternative |
| Remove Antiseizure Meds | all antiseizure meds including CBD | Sedation assisted | | | |
| Vasodilation | Dobutamine (preferred) | low dosage | normal dosage | normal dosage | normal dosage |
| Vasodilation | Prostin (special cases) | low dosage | normal dosage | normal dosage | Dobutamine |
| Measure Blood-Oxygen levels | case & situation-specific oxygenation | | | | |
| Oxygenation (inhalation mask) | Ipratropium (anticholinergic-if needed) | | during sedation | | during sedation |
| Oxygenation (inhalation mask) | Tiotropium (anticholinergic-if needed) | | during sedation | | during sedation |
| Oxygenation (inhalation mask) | Aclidinium (anticholinergic-if needed) | | during sedation | | during sedation |
| Oxygenation (short duration) | Albuterol (bronchial relaxant) | | constant IV | | constant IV |
| Oxygenation (short-duration) | Levalbuterol (bronchial relaxant) | | constant IV | | constant IV |
| Oxygenation (long-duration) | Arformoterol (respiratory impairments) | | | twice daily | twice daily |
| Oxygenation (long-duration) | Salmeterol (respiratory impairments) | | | twice daily | twice daily |
| Oxygenation (long-duration) | Xanthine (respiratory impairments) | | | twice daily | twice daily |
| Oxygenation (long-duration) | Indacaterol (respiratory impairments) | | | twice daily | twice daily |
| Oxygenation (long-duration) | Formoterol (respiratory impairments) | | | twice daily | twice daily |
| Oxygenation (long-duration) | Vilanterol (respiratory impairments) | | | twice daily | twice daily |
| Immunoinflammatory | Cyclophosphamide (Cytoxan) | twice daily | | | twice daily |
| Immunoinflammatory | Ketoprofen | | | twice daily | twice daily |
| Amino Acid Supplement | IV or Oral | daily | daily | daily | daily |

Midazolam Deep-Quiet Chart

| | Midazolam Deep-Quiet Chart Midazolam extended sedation deep-quiet session | | | | | |
|---|---|---|---|---|---|---|
| Body-weight | Day one of sedation | Day two of sedation | Day three of sedation | Day four of sedation | Day five of sedation | Day six of sedation |
| First Dose | 0.5 mcg/kg/minute | 1 mcg/kg/minute | 2 mcg/kg/minute | 3 mcg/kg/minute | 4 mcg/kg/minute | 5 mcg/kg/minute |
| 5 kg | 0.15 mL per hour | 0.3 mL per hour | 0.6 mL per hour | 0.9 mL per hour | 1.2 mL per hour | 1.5 mL per hour |
| 10 kg | 0.3 mL per hour | 0.6 mL per hour | 1.2 mL per hour | 1.8 mL per hour | 2.4 mL per hour | 3.0 mL per hour |
| 15 kg | 0.45 mL per hour | 0.9 mL per hour | 1.8 mL per hour | 2.7 mL per hour | 3.6 mL per hour | 4.5 mL per hour |
| 20 kg | 0.6 mL per hour | 1.2 mL per hour | 2.4 mL per hour | 3.6 mL per hour | 4.8 mL per hour | 6.0 mL per hour |
| 25 kg | 0.75 mL per hour | 1.5 mL per hour | 3.0 mL per hour | 4.5 mL per hour | 6.0 mL per hour | 7.5 mL per hour |
| 30 kg | 0.9 mL per hour | 1.8 mL per hour | 3.6 mL per hour | 5.4 mL per hour | 7.2 mL per hour | 9.0 mL per hour |
| 35 kg | 1.05 mL per hour | 2.1 mL per hour | 4.2 mL per hour | 6.3 mL per hour | 8.4 mL per hour | 10.5 mL per hour |
| 40 kg | 1.2 mL per hour | 2.4 mL per hour | 4.8 mL per hour | 7.2 mL per hour | 9.6 mL per hour | 12.0 mL per hour |
| 45 kg | 1.35 mL per hour | 2.7 mL per hour | 5.4 mL per hour | 8.1 mL per hour | 10.8 mL per hour | 13 mL per hour |
| 50 kg | 1.50 mL per hour | 3.0 mL per hour | 5.0 mL per hour | 9.0 mL per hour | 12.0 mL per hour | 15 mL per hour |
| 55 kg | 1.65 mL per hour | 3.3 mL per hour | 6.6 mL per hour | 9.9 mL per hour | 13.2 mL per hour | 16.5 mL per hour |
| 60 kg | 1.8 mL per hour | 3.6 mL per hour | 7.2 mL per hour | 1.08 mL per hour | 14.4 mL per hour | 18.0 mL per hour |

IV. Resolving Neurological and Nervous System Bioelectrical Dysregulation and Remyelinating Embodiments of the inventive concept include Dobutamine as a prescriptible injection or intravenous delivery or via ingestible formulation for compensation of deficiencies in vasodilation and for fueling glial cells via robust blood-flow and reducing oxygen-starved neuronal agitation.

Other embodiments of the inventive concept include using sedation, such as provided by Neuroquiescence, for a minimum of three days while ensuring robust bloodflow for fueling brain or central nervous system or neuromuscular repairs.

In yet other embodiments of the inventive concept, Dobutamine can also be used as a prophylaxis for about any neurological dysfunction. This is indicated by studies showing that most neurological dysfunctions have vascular roots; refer to FIG. 1 of the cycle of causes and effects. Neurological dysfunctions that may be treated according to embodiments of the present inventive concept include, for example: Epilepsy; seizures; Infantile Spasms; Essential Tremors; Essential Palatal Tremors; Hemiplegia; Parkinson's; Blepharospasms; Nystagmus; Ménière; Fibromyalgia; Multiple Sclerosis; Longevity; Myalgic Encephalomyelitis (Chronic Fatigue Syndrome); Guillain-Barre Syndrome; Chronic Inflammatory Demyelinating Polyneuropathy; Amyotrophic Lateral Sclerosis; Cluster and Migraine Headaches; Peripheral Pain; Restless Leg Syndrome; Phantom-limb Pain; Myasthenia Gravis; Rett Syndrome; Mitochondrial Disease; GLUT1 Deficiency Syndrome; Pyruvate Dehydrogenase Complex Deficiency; Spinal Axonal Repair; Spinal Surgery Recovery; Hippocam pal Memory Retrieval Deficits; Lewy body Dementia; Attention Deficit Disorder and Attention Deficit Hyperactivity Disorder; Autism and Asperger's; Depression; Post-Traumatic Stress Disorders; Chronic Anxiety; Nightmares and disruptive sleep disorders; Impulsivity; Compulsivity; Inattentiveness; Addictive Soothing Behaviors; Eating Disorders, e.g., Anorexia Nervosa; Chemical Addictions, e.g., alcohol, Opioid; Nicotine, and/or Methamphetamine addiction; Human alcohol-related neuropathology; Dementia; Alzheimer's; Schizophrenia; Bipolar Disorder; Obsessive-Compulsive Disorder; Psychosis; Auditory Agnosia; Hyperacusis; Tinnitus; Auditory Neuropathy; Stuttering of Speech; Speech Tics; Tourette's; Cerebral Palsy; Acute Respiratory Distress Syndrome; Neuromuscular Disorders; Seizures from Neurosurgery; Benign Rolandic Epilepsy of Childhood; Benign Familial Neonatal Infantile Seizures; Absence Epilepsy; Juvenile Myoclonic Epilepsy; Benign Occipital Epilepsy; Lennox-Gastaut Syndrome Epilepsy; SCN2A encephalopathy; Myoclonic Astatic Epilepsy; and Narcolepsy.

According to embodiments of the inventive concept, traits of Autism may be resolved using the full Neuroquiescence protocol for remyelination, and then with patients having maintenance Dobutamine to compensate for the genetic mutation 16p11.2.

Similar results are predicted with most genetic predispositions for Epilepsy, Fibromyalgia, Alzheimer's and other manifestations of neuronal agitation and demyelinating dysfunctions.

V. Dobutamine for Resolving Neurological and Nervous System Bioelectrical Dysregulation and Demyelination Dobutamine repackaging and repurposing will enable medical doctors to prescribe Dobutamine injections for their patients. This may be similar to present distribution and availability of dosages and injectors of Insulin from our local pharmacy stores.

The traditional "intractable" Epilepsy concept is overcome by use of Dobutamine, which is about cerebrovascular bloodflow, not about suppression of seizures. Dobutamine outperforms antiseizure medications because it addresses the true root-cause of seizures.

Dobutamine consistently outperformed their antiseizure medication even though neuronal agitation was still present for the weeks of microvascular preparation for full remyelination.

Adult use of intravenous Dobutamine for patients who previously were taking multiple antiseizure medications become seizure free even before their sedation session for remyelination. An adult with unmanageable morning seizures for fifteen years became seizure-free in less than one month, then removed all antiseizure medications, and with a few more months has no neuronal agitation measurable at EEG sensitivities.

For seizure patients, Dobutamine alone will rarely replace for the full remyelination of Neuroquiescence; however, the Dobutamine can produce a profound change in quality of life for patients and their families, an escape from antiseizure medications. Rather than antiseizure management medications, patients awaiting Neuroquiescence can have a daily injection of Dobutamine.

Dobutamine can also be used as a prophylaxis for all neurological dysfunctions on our list. This is implied by studies showing that most neurological dysfunctions have vascular roots; again, refer to our chart of the cycle of causes and effects.

Children with symptoms of ADHD would have daily dobutamine injections; after a few weeks of reduction in symptoms, their ADHD medication would be withdrawn as they await capacity for their Neuroquiescence deep quiet sedation session. Note that we have a psychiatrist who has already noticed that after children had their tonsils removed, their ADHD symptoms vanished for two to three weeks, then they would return. We have no doubts that ADHD is low-hanging fruit for the protocol proven to resolve the neuronal agitation and demyelination of Epilepsy.

Improving cerebrovascular bloodflow increases neuroplasticity for deep brain region connectivity associated with self-control and impulsivity. Although the Dobutamine-prepared sedation session of Neuroquiescence is required to achieve maximum remyelination of agitated neurons, we expect that daily Dobutamine injections will enable meaningfully reduced impulsivity in the bidirectional relationship between emotionality and nervous system agitation as a root of addictive soothing.

Adults around age 60 might be prescribed a daily Dobutamine injection to protect their blood-brain barrier, thereby providing a prophylaxis for Alzheimer's. They still might need Neuroquiescence to resolve their agitated neurons, which will reduce other risks as well such as peripheral pains. Animal studies have shown that agitated neurons reduce lifespan. Daily Dobutamine injections will, we predict, improve robustness of health all thanks to better bloodflow in lungs and brain for reductions in neurocognitive degeneration, and will reduce organ failure and neuromuscular degeneration that has been associated with aging.

Use of Dobutamine during any sustained sedation would avoid the neurocognitive and neuromuscular degeneration experienced during extended ventilation equipment use in cases such as treatment for the coronavirus. Sedation without managing blood viscosity and robustness of oxygenation to glial cells will increase risks. Sedation with intravenous Dobutamine reduces blood viscosity for better access to microvessels while also reducing the loading on heart function.

Neuronal Agitation

Deficiencies in microvascular bloodflow defuel glial cells and cause astrocytes to agitate neurons to invest their energy in bioelectrical signaling to stimulate vascular support, bringing vascular transport of oxygen.

This neuronal agitation serves a purpose for their survival. If the neuron's need for more oxygenation through bloodflow becomes quenched, the bioelectrical agitation was successful, and the neuron becomes stable. If there is a delay in successful oxygenation of an agitated neuron, the bioelectrical agitation may stimulate even well-oxygenated neurons to connect in unproductive circuits without appropriate inhibitory and excitatory links.

The bioelectrical pulsing synchronizes within the interconnected cluster of neurons, thereby increasing the amplitude of the neuroelectromagnetic field measured on an electroencephalogram (EEG). There may be few neurons agitated by low bloodflow and deficient oxygenation, but their interconnected circuit of synchronized hyperactivity exhausts the bloodflow supply of oxygen which may stress vascular capacity and leave other neurons in an oxygenation deficit.

Cerebrovascular resilience supports oxygenation of neurons. Deficiencies in cerebral bloodflow or microvascular support of neurons increases their agitated activity. Neuronal agitation activity exhausts oxygen levels which are already low, and surrounding neurons become agitated. Febrile illness or strenuous exercise when in a constricted bloodflow state can induce exhaustion of oxygen levels at the neurons thereby stimulating neuronal agitation. Inconsistent microvascular transport of oxygen increases inflammation around the neurons thereby inhibiting potential healing.

Immunoinflammatory imbalance associated with diminished oxygenation during sleep is a threat to neuronal health. Oxygen transfer deficiencies in lungs to vascular transport and into microvascular support of neurons decreases during sleep thereby increasing risks of seizures. During sleep, autoregulation reduces bloodflow which increases risk of low oxygenation to neurons which may be above the threshold needed to avoid agitation during the day. Sleep issues such as restless leg syndrome may be indicative of deficiencies in oxygenation to the sensory neurons in the legs, and over time these neurons may become hyperactive and produce sustained itchiness or other symptoms.

As with the root-cause of epilepsy, the central nervous system influenced by immunological and vascular distress stimulate neurons outside the brain to agitation. Resolving these root-causes and the neurovascular inflammation around the central nervous system is required to potentially provide healing, otherwise those neurons will again over time become noisy, resulting in pain and other signaling dysregulations.

VI. Bloodflow and Neuroquiescence

Neuroquiescence is a method that enables the brain to resolve its own Epilepsy. Up until now, the only neurological dysfunction fully and well proven to be resolved by Neuroquiescence is Epilepsy. Independent studies by neurobiology researchers are recognizing the vascular roots of brain and nervous system dysregulation commonalities among neurological dysfunctions previously thought to be completely unrelated. These independent studies justify expectations that Neuroquiescence will, for many neurological conditions, provide entirely the solution as with Epilepsy, or an enabling part if for a combination therapy.

The objective of this treatment protocol is to avail effective fueling of glial cells while pausing neuronal bioelectrical activity to enable remyelination, disconnecting dysfunctional neuronal connections, and resetting cellular homeostasis.

While glial cells persistently strive to accomplish remyelination during normal neuronal function, especially during sleep, glial cells are bloodflow-deprived during a nearby neuronal dysregulated state of saturated bioelectrical activity, so remyelinating and neuronal pruning cannot occur. Achieving remyelination for neurons experiencing bioelectrical dysregulation requires that their bioelectrical activity be paused, hence our calling this protocol "Neuroquiescence."

Protocols of the present inventive concept resolve vascular impediments to robust bloodflow to microvessels for oxygenation of neurons and glial cells, and then with bioelectrical pause of neuronal activity, avails glial cells accelerated remyelination.

An innovative conceptualization of the root-cause as a sequence of neurovascular events that produce seizures associated with Epilepsy enabled the development of the present inventive concept. FIG. 1 depicts the loop of dysfunctional causes and effects of neurovascular events in disorders involving neurological and nervous system bioelectrical dysregulation.

Neuroquiescence enabling the brain to fully repair and resolve its own Epilepsy may be best explained as a sequence of neurovascular events that produce seizures of Epilepsy and other neurodevelopmental and neurodegenerative dysfunctions.

This loop of causes and effects can be entered at any point; for example, neuroinflammation induced by a febrile illness or a traumatic brain injury could happen first. For babies who develop Epilepsy, the low oxygenation is likely to happen first. Regardless of where the cycle begins, the neurovascular sequence of dysfunctional causes and effects loops indefinitely until it is disrupted. Neuroquiescence disrupts this cycle first by stimulating robust cerebrovascular bloodflow and repairing the BBB blood-brain barrier in preparation for fueling glial cells for remyelination.

Neuronal bioelectrical activity evokes neurovascular coupling for stimulating bloodflow. Deficiencies in neurovascular coupling or oxygen with bloodflow may trigger the deprived neuron to produce bioelectrical pulses independent of any neuronal circuit inputs. This "neuronal agitation" ensures the survival of the neuron if successful vasodilation is restored, but if the bloodflow deprivation continues, neuronal agitation calling for increased bloodflow is fundamental to bioelectrical dysregulation leading to demyelination.

Neuronal agitation produces neuronal noise from the computational perspective, reducing the efficiency of brain circuits. For sensory neurons, neuronal noise may produce the perception of pain, or in the cause of Tinnitus, the perception of sound that does not correlate with acoustic inputs. For noisy neuromuscular control in the feedback loop, the more the brain strives to steady the tremor, the greater the error in the noisy muscular correction.

Neurobiological studies on neuronal noise and agitated neurons in the neurovascular coupling mechanisms expose part of the intersystem dependencies associated with vascular roots of neurological dysfunction.

Neurobiological studies on demyelination in Autism, Alzheimer's, Fibromyalgia, Post Traumatic Stress Disorder, and Addictions along with their overactive or agitated neurons place these along with Epilepsy as among the neurodevelopmental and neurodegenerative dysfunctions expected to be resolved or assisted by improving immunovascular robustness and then enabling by sustained sedation a biomechanism of glial cells for neuronal repairs.

Having described various aspects of the present inventive concept, the same will be explained in further detail in the following examples, which are included herein for illustration purposes only, and which are not intended to be limiting to the inventive concept.

EXAMPLE 1

Case Examples

We have had approximately 200 cases between the two hospitals using the protocol to resolve epilepsy. We deliberately sought out difficult cases, which was the reason for adding the second hospital in a large city. There were over twenty patients living in the hospital because their seizures were so uncontrollable and risky. All of these patients were resolved of their seizures, so we sought teenagers to be brought into the hospital. In all, three cases of epilepsy of the approximately 200 are not resolved. A fourth has diabetes which is the root-cause of the seizures and must be resolved before we can heal the neuronal connections causing the seizures.

Case Example: JH

An age eight-months baby presented brain malformation and diminished oxygenation and bloodflow in the left hemisphere.

Parents noted at four months abnormal movements which we attribute to muscular spasms, especially for the left hand.

EEG measurement indicated monomorphic high amplitude neuronal activity, but not interconnected with a region that would trigger seizures.

In this case we used for treatment only Vasodilation Pediatric Prostin VF—0.05-01 mcg/kg/min IV initially at week one and usual maintenance ranges from 0.01-0.4 mcg/kg/min for six weeks.

All symptoms of Infantile Spasms were resolved. EEG measurements became normal within three days, and cerebral bloodflow measurements became normal within six weeks.

To assist with good neurovascular healing, the patient had twice daily IV sessions of vasodilation medication, oxygenation medication, and an amino acid for approximately one year. EEG measurements were made for one hour during the twice-daily IV medications. fMRI brainscans and measurements of cerebral bloodflow were scheduled twice per week for the first year, and once each month thereafter along with an EEG measurement session.

Case Example: JAS

An age nine-months baby presented recurrent seizures twice daily as left hemisphere focal brain agitation bioelectrical activity. She had her first convulsive episode at age of two months during a febrile illness.

There is a family history, a cousin with a history of "grand mal" seizures who died at age 3. A well-nourished infant, she presented inconsolable irritability requiring attention. She had a history of attempts with ineffective antiseizure medications.

Cerebral bloodflow was within normal ranges. During sleep, EEG amplitudes indicated epileptic levels of bioelectrical activity exceeding 85% of spatial tracing. The brain imaging revealed a ventricular enlargement center of high amplitude bioelectrical activity. She had a radiation session which presented good prognostic following the ventricular embolism surgical intervention with easy access.

In this case we used for treatment Vasodilation Pediatric Prostin VF—0.05-01 mcg/kg/min by IV initially at week one. Usual maintenance ranges from 0.01-0.4 mcg/kg/min for six weeks.

As with all children, in all cases, we removed all antiseizure medications.

Daily Amino Acid 12 mcg/kg (maximum dose) for six weeks. Daily Glucosamine oral supplements for children; (the glucosamine was later removed from the protocol).

Midazolam continuous infusion initially 50-100 mcg/kg IV over 2-3 minutes, repeat q2-3 min PR. Required up to 600 mcg/kg total dose; we did not exceed 6 mg total dose for four days. Neuroquiescence sessions with Midazolam were repeated twice before showing total improvement and healing. All symptoms of seizures and agitated bioelectrical brain activity were resolved. EEG monitoring and Brainscans became normal and her learning assessments are considered developmentally good.

Case Example: LIL

A child of age four-years with episodes of "blanking-out" has episodes in which abruptly stops all activity for 10 seconds, followed by a rapid return to full consciousness. Her eyes are open during the episodes and she remains motionless with occasional hand movements.

History of previous ineffective antiseizure medications was Tegretol for 2 years. Radiologic brain examination revealed epileptic activity in sleep time. Normal cerebral blood flow (CBF).

General physical examination revealed an allergy for Midazolam. In this case we used for treatment Fentanyl as an alternative medication for Neuroquiescence.

We investigated her bloodflow and oxygenation with brainscans during her sleep, and we found normal cerebral bloodflow, but low oxygen levels in the brain. As such, Prostin was used as the vasodilator for assisting the microvessels.

Vasodilation Pediatric Prostin VF—0.05-01 mcg/kg min IV initially at week one. Usual maintenance ranges from 0.01-0.4 mcg/kg/min for six weeks.

All antiseizure medications were removed. Daily Amino Acid 12 mcg/kg (maximum dose) for six weeks. Daily Glucosamine oral supplements for children; (we later removed glucosamine from the protocol).

Fentanyl premedication 0.5-2 mcg/kg IV gives 3 minutes prior the anesthesiologist proceeded for the more maximum safe dosage on keeping her for continuous sedation. After premedication we adjusted Fentanyl dosage 2-3 mcg/kg IV/IMq1-2 hr PRN. We did not exceed 6 mg total dose for six days. Neuroquiescence with Fentanyl was repeated for three sessions before showing total improvement and healing.

All symptoms of noisy bioelectrical brain activity after Neuroquiescence were resolved. EEG monitoring and brainscans became normal and her learning assessment post-treatment are considered appropriated for her age.

Case Example: REM

An age eleven-months baby presented with low neuronal agitation recurrent from the left hemisphere.

The first EEG-measured bioelectrical agitation was measured at age four months. There were no seizures, but antiseizure medication had been attempted to resolve the agitated neurons to prevent seizures.

General physical examination revealed a well-nourished infant with normal baseline oxygenation measurement and cerebral bloodflow.

The neurological examination revealed an alert infant. Radiologic brain imagining examination revealed low-amplitude agitation activity especially during sleep.

In this case we used for treatment only Vasodilation Pediatric Prostin VF—0.05-01 mcg/kg min IV initially at week one. Usual maintenance ranges from 0.01-0.4 mcg/kg/min for six weeks.

We removed all previous antiseizure medications (which were GABA-based).

Daily Amino Acid 12 mcg/kg (maximum dose) for six weeks, and Daily Glucosamine oral supplements for children. (The glucosamine was later discontinued from the protocol.)

All symptoms of bioelectrical agitation activity were resolved following the vasodilation treatment, so in this case there was no need for a Neuroquiescence session.

EEG monitoring and brainscans became normal and his learning and interaction assessment post-treatment are considered normal for his age.

Case Example: BAR

An age three-years boy was presented to his pediatrician with a history of new-onset headaches accompanied by nausea lasting for several hours daily. The neurological examination was normal, and migraine was initially suspected.

After symptoms persisted for two weeks, he presented refractory seizures that began with his typical aura followed by lip-smacking and left-hand automatisms; the right-hand had a tonic posture. He had a brief post-ictal aphasia.

Cranial magnetic resonance imaging (MRI) revealed a cerebral mass located in the pineal region measuring 1×2.2×2.5 cm. The tumor displayed dorsal cystic structures and a ventral solid portion with inhomogeneous contrast agent enhancement leading to a compression of the tectum. The consecutive aqueduct stenosis resulted in occlusive hydrocephalus. ventriculostomy of the third ventricle was performed to reduce intracranial pressure.

Tumor markers such as cavernous angioma in serum and cerebrospinal fluid (CSF) were within the normal range.

We oversaw the patient through a total tumor resection through a suboccipital supra cerebellar approach. Postoperative imaging demonstrated complete reception. Postoperative clinical examination, the boy was found to have several episodes of seizures per day recurrent from both hemispheres and high bioelectrical agitation measured with EEG.

In this case we used for treatment Vasodilation Pediatric Prostin VF—0.05-01 mcg/kg min IV initially at week one. Usual maintenance ranges from 0.01-0.4 mcg/kg/min for six weeks.

Daily Amino Acid 12 mcg/kg (maximum dose) for six weeks.

Daily Glucosamine oral supplements for children (which is no longer in the protocol).

Anti-inflammatory medications from week one per the standard alternating weeks.

As for all children, in all cases, all antiseizure medications were removed.

Neuroquiescence with Midazolam continuous infusion initially 50-100 mcg/kg IV over 2-3 minutes, repeat q2-3 min PR. Required up to 600 mcg/kg total dose; we did not exceed 6 mg total dose for seven days. Neuroquiescence with Midazolam was repeated several seven-day-sessions before showing an improvement in his noisy bioelectrical brain activity.

All symptoms of seizures and bioelectrical brain activity after Neuroquiescence showed a partial improvement. He has continuous treatment, EEGs, Brainscans and fMRI.

Neuroinflammation is the likely impediment to healing. The next step is to use a stronger anti-inflammation medication, which will require permission for a trial inasmuch as it is not presently approved for children.

Example Case: STEH

Early encephalopathy, beginning in the first month of life, associated with inborn errors of metabolism by hyperglycemia. Ineffective antiseizure medications and treatments fill his 14 years of life.

Family history notes that his father had similar episodes as a child.

Radiologic brain examination revealed epileptic activity. Normal cerebral blood flow (CBF). EEG epileptic activity spatially exceeding 90% of the tracing, especially under photo stimulation. The brain imaging revealed a moderately-high amplitude of agitated bioelectrical activity. He had severe myoclonus, focal and tonic crises.

In this case we used for treatment Vasodilation Prostin VF—0.05-01 mcg/kg min IV initially at week one. Usual maintenance ranges from 0.01-0.4 mcg/kg/min for six weeks. We removed all antiseizure medications.

Daily Amino Acid 12 mcg/kg (maximum dose) for six weeks.

Daily Glucosamine oral supplements for children

Anti-inflammation medication per the standard schedule in alternating weeks.

Neuroquiescence with Midazolam continuous infusion initially 50-100 mcg/kg IV over 2-3 minutes, repeat q2-3 min PR. Required up to 600 mcg/kg total dose; we did not exceed 6 mg total dose for seven days. Neuroquiescence with Midazolam was repeated for two sessions before showing total improvement and healing.

All symptoms of seizures and bioelectrical brain activity were resolved after Neuroquiescence. EEG monitoring and Brainscans became normal and his learning assessment post-treatment are considered normal.

His psychological assessment revealed a continuous behavioral maladaptation to pretend to exhibit the symptoms as when he had seizures, but only when his mother is present. He performs for her even though we can see on EEG that not only has he no seizure, he has no neuronal agitation. We expected to see this in some older patients, and we did. With Neuroquiescence able to resolve seizures and completely heal epilepsy, developmental psychology will be needed for helping minds that never developed emotionally and/or intellectually to their genetic potential.

EXAMPLE 2

Drug Guideline: Dobutamine

Summary:

Dobutamine is a synthetic catecholamine that stimulates beta (β) receptors of the heart to produce mild chronotropic, hypertensive, arrhythmogenic and vasodilation effects. It is used in the ICU for acute heart failure, cardiogenic, shock, pulmonary edema and to increase cardio output.

Dobutamine 250 mg vial (Protect from Light)

Administration:

Reconstitute vial with 10 mLs of water for injection, 0.9% sodium chloride should not be used to reconstitute vial but may be used for further dilution Add 250 mg dobutamine to 40 mLs sterile 0.9% sodium chloride, to give a final volume of 50 ml and final concentration of 5 mg/mL, or 5000 micrograms/mL Desired dose range is 2.5-15 micrograms/kg/minute To Calculate Rate—DOBUTAMINE Dose (microgram/kg/min)×weight×60 (min/hr)÷strength (micrograms/ml)=rate (ml/hr)

e.g. 2.5 microgram/kg/min×100 kg×60 min/hr=15,000÷5000 microgram/ml=3 ml/hr

To Calculate Dose—DOBUTAMINE:

Strength (micrograms/ml)×rate (ml/hr)÷weight (kg)÷60 (min/hr)=dose (microgram/kg/min) delivered e.g. 5000 mcg/ml×3 ml/hr÷100 kg÷60 min/hr=2.5 micrograms/kg/min Titrate the infusion using parameters which have been discussed and documented on the management plan with the Medical Officer, including:

Mean arterial blood pressure

Cardiac index

Pulmonary capillary wedge pressure (PCWP)

Systemic vascular resistance

If necessary, increase the infusion by 1 microgram/kg/min every 5 minutes, while closely monitoring the patient for the desired effect.

Hypotension may follow the administration of dobutamine

Rate of Dobutamine delivery for adults is shown in the following table:

Dobutamine Rate Calculation Table

TABLE

DOBUTAMINE RATE CALCULATION

| Mcg/kg/min | 50 kg | 55 kg | 60 kg | 65 kg | 70 kg | 75 kg | 80 kg | 85 kg | 90 kg | 95 kg | 100 kg | 105 kg | 110 kg | 115 kg | 120 kg |
|---|---|---|---|---|---|---|---|---|---|---|---|---|---|---|---|
| 1.0 | 0.6 | 0.7 | 0.7 | 0.8 | 0.8 | 0.9 | 1.0 | 1.0 | 1.1 | 1.1 | 1.2 | 1.3 | 1.3 | 1.4 | 1.4 |
| 1.5 | 0.9 | 1.0 | 1.1 | 1.2 | 1.3 | 1.4 | 1.4 | 1.5 | 1.6 | 1.7 | 1.8 | 1.9 | 2.0 | 2.1 | 2.2 |
| 2.0 | 1.2 | 1.3 | 1.4 | 1.6 | 1.7 | 1.8 | 1.9 | 2.0 | 2.2 | 2.3 | 2.4 | 2.5 | 2.6 | 2.8 | 2.9 |
| 2.5 | 1.5 | 1.7 | 1.8 | 2.0 | 2.1 | 2.3 | 2.4 | 2.6 | 2.7 | 2.9 | 3.0 | 3.2 | 3.3 | 3.5 | 3.6 |
| 3.0 | 1.8 | 2.0 | 2.2 | 2.3 | 2.5 | 2.7 | 2.9 | 3.1 | 3.2 | 3.4 | 3.6 | 3.8 | 4.0 | 4.1 | 4.3 |
| 3.5 | 2.1 | 2.3 | 2.5 | 2.7 | 2.9 | 3.2 | 3.4 | 3.6 | 3.8 | 4.0 | 4.2 | 4.4 | 4.6 | 4.8 | 5.0 |
| 4.0 | 2.4 | 2.6 | 2.9 | 3.1 | 3.4 | 3.6 | 3.8 | 4.1 | 4.3 | 4.6 | 4.8 | 5.0 | 5.3 | 5.5 | 5.8 |
| 4.5 | 2.7 | 3.0 | 3.2 | 3.5 | 3.8 | 4.1 | 4.3 | 4.6 | 4.9 | 5.1 | 5.4 | 5.7 | 5.9 | 6.2 | 6.5 |
| 5.0 | 3.0 | 3.3 | 3.6 | 3.9 | 4.2 | 4.5 | 4.8 | 5.1 | 5.4 | 5.7 | 6.0 | 6.3 | 6.6 | 6.9 | 7.2 |
| 5.5 | 3.3 | 3.6 | 4.0 | 4.3 | 4.6 | 5.0 | 5.3 | 5.6 | 5.9 | 6.3 | 6.6 | 6.9 | 7.3 | 7.6 | 7.9 |
| 6.0 | 3.6 | 4.0 | 4.3 | 4.7 | 5.0 | 5.4 | 5.8 | 6.1 | 6.5 | 6.8 | 7.2 | 7.6 | 7.9 | 8.3 | 8.6 |
| 6.5 | 3.9 | 4.3 | 4.7 | 5.1 | 5.5 | 5.9 | 6.2 | 6.6 | 7.0 | 7.4 | 7.8 | 8.2 | 8.6 | 9.0 | 9.4 |
| 7.0 | 4.2 | 4.6 | 5.0 | 5.5 | 5.9 | 6.3 | 6.7 | 7.1 | 7.6 | 8.0 | 8.4 | 8.8 | 9.2 | 9.7 | 10.1 |
| 7.5 | 4.5 | 5.0 | 5.4 | 5.9 | 6.3 | 6.8 | 7.2 | 7.7 | 8.1 | 8.6 | 9.0 | 9.5 | 9.9 | 10.4 | 10.8 |
| 8.0 | 4.8 | 5.3 | 5.8 | 6.2 | 6.7 | 7.2 | 7.7 | 8.2 | 8.6 | 9.1 | 9.6 | 10.1 | 10.6 | 11.0 | 11.5 |
| 8.5 | 5.1 | 5.6 | 6.1 | 6.6 | 7.1 | 7.7 | 8.2 | 8.7 | 9.2 | 9.7 | 10.2 | 10.7 | 11.2 | 11.7 | 12.2 |
| 9.0 | 5.4 | 5.9 | 6.5 | 7.0 | 7.6 | 8.1 | 8.6 | 9.2 | 9.7 | 10.3 | 10.8 | 11.3 | 11.9 | 12.4 | 13.0 |
| 9.5 | 5.7 | 6.3 | 6.8 | 7.4 | 8.0 | 8.6 | 9.1 | 9.7 | 10.3 | 10.8 | 11.4 | 12.0 | 12.5 | 13.1 | 13.7 |
| 10 | 6.0 | 6.6 | 7.2 | 7.8 | 8.4 | 9.0 | 9.6 | 10.2 | 10.8 | 11.4 | 12.0 | 12.6 | 13.2 | 13.8 | 14.4 |
| 10.5 | 6.3 | 6.9 | 7.6 | 8.2 | 8.8 | 9.5 | 10.1 | 10.7 | 11.3 | 12.0 | 12.6 | 13.2 | 13.9 | 14.5 | 15.1 |
| 11.0 | 6.6 | 7.3 | 7.9 | 8.6 | 9.2 | 9.9 | 10.6 | 11.2 | 11.9 | 12.5 | 13.2 | 13.9 | 14.5 | 15.2 | 15.8 |
| 11.5 | 6.9 | 7.6 | 8.3 | 9.0 | 9.7 | 10.4 | 11.0 | 11.7 | 12.4 | 13.1 | 13.8 | 14.5 | 15.2 | 15.9 | 16.6 |
| 12.0 | 7.2 | 7.9 | 8.6 | 9.4 | 10.1 | 10.8 | 11.5 | 12.2 | 13.0 | 13.7 | 14.4 | 15.1 | 15.8 | 16.6 | 17.3 |
| 12.5 | 7.5 | 8.3 | 9.0 | 9.8 | 10.5 | 11.3 | 12.0 | 12.8 | 13.5 | 14.3 | 15.0 | 15.8 | 16.5 | 17.3 | 18.0 |
| 13.0 | 7.8 | 8.6 | 9.4 | 10.1 | 10.9 | 11.7 | 12.5 | 13.3 | 14.0 | 14.8 | 15.6 | 16.4 | 17.2 | 17.9 | 18.7 |
| 13.5 | 8.1 | 8.9 | 9.7 | 10.5 | 11.3 | 12.2 | 13.0 | 13.8 | 14.6 | 15.4 | 16.2 | 17.0 | 17.8 | 18.6 | 19.4 |
| 14.0 | 8.4 | 9.2 | 10.1 | 10.9 | 11.8 | 12.6 | 13.4 | 14.3 | 15.1 | 16.0 | 16.8 | 17.6 | 18.5 | 19.3 | 20.2 |
| 14.5 | 8.7 | 9.6 | 10.4 | 11.3 | 12.2 | 13.1 | 13.9 | 14.8 | 15.7 | 16.5 | 17.4 | 18.3 | 19.1 | 20.0 | 20.9 |
| 15.0 | 9.0 | 9.9 | 10.8 | 11.7 | 12.6 | 13.5 | 14.4 | 15.3 | 16.2 | 17.1 | 18.0 | 18.9 | 19.8 | 20.7 | 21.6 |

EXAMPLE 3

Anesthetic Administration

Figure 2:
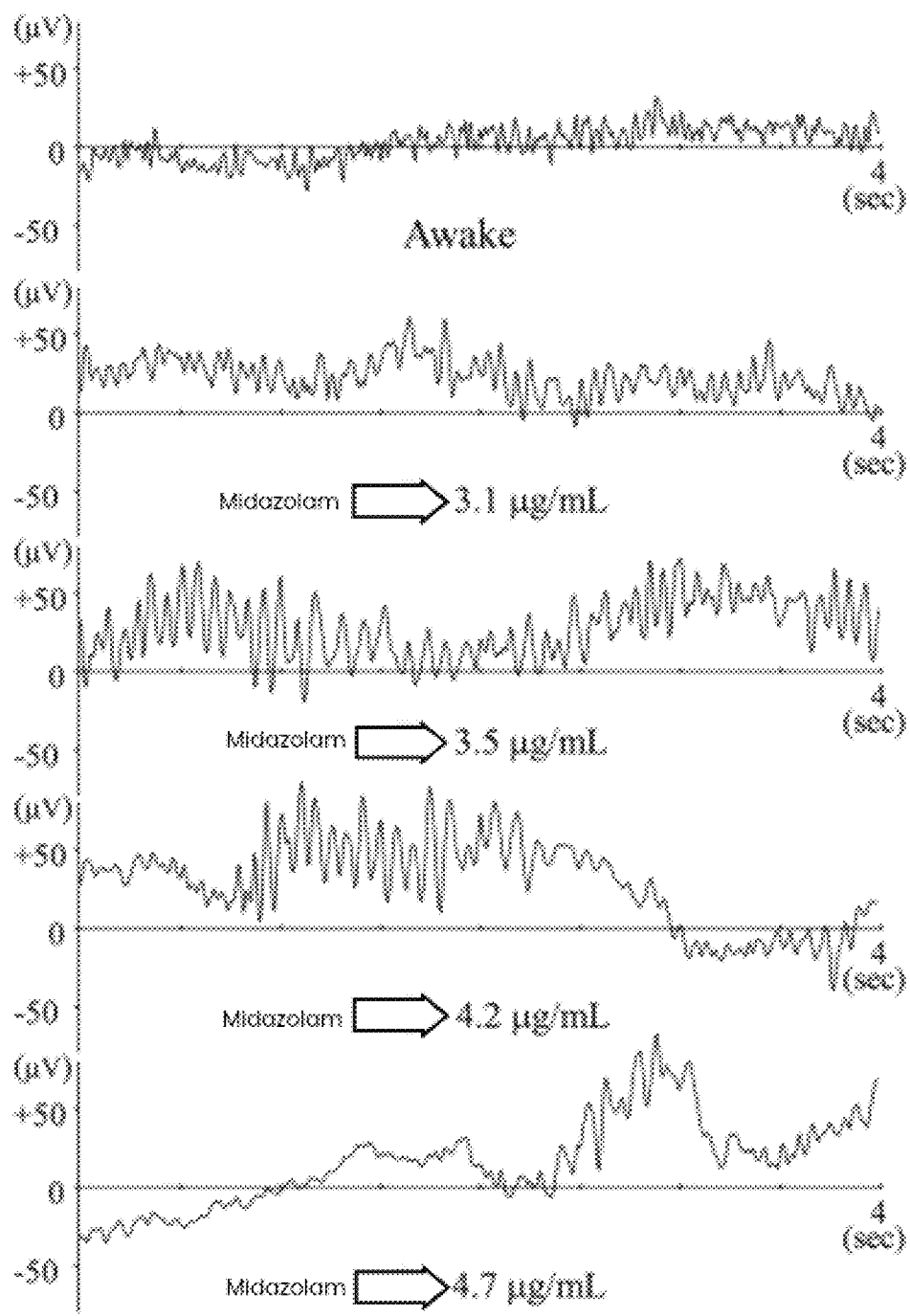
FIGS. 2 and 3 depict electroencephalograms (EEGs) of a patient undergoing deep sedation and recovery using general anesthesia.
Figure 3:
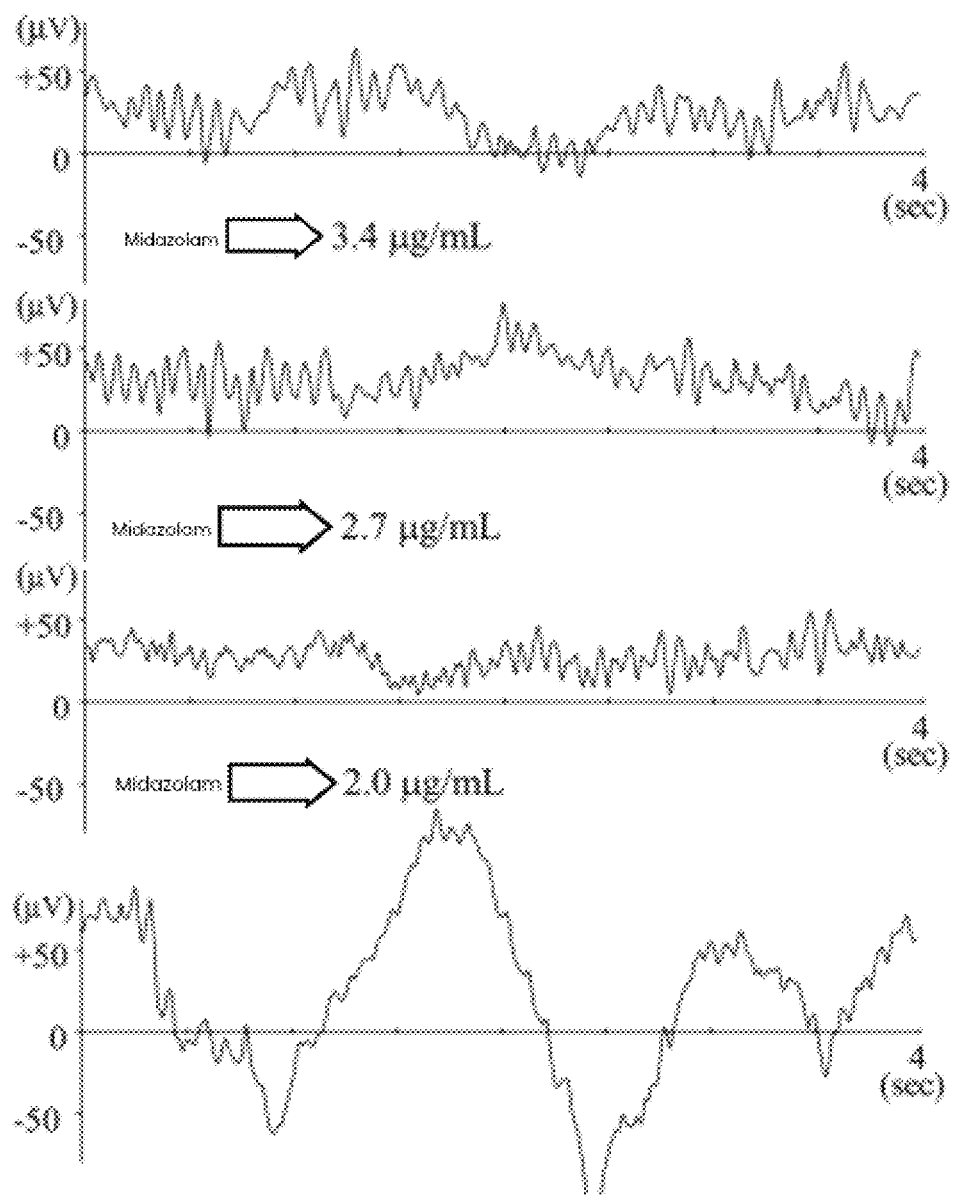
Figure 4:
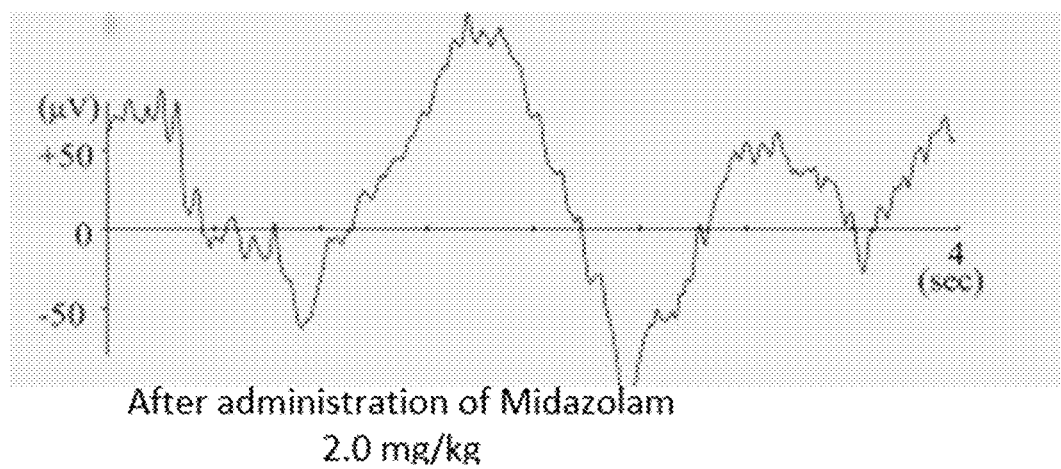
FIG. 4 depicts an electroencephalogram (EEG) of a patient under sedation after anesthesia administration.

Electroencephalograms (EEGs) of patients being administered a general anesthetic, e.g., midazolam, and monitoring EEGs from awake to deep sedation, and recovery are depicted in FIGS. 2 and 3. An electroencephalogram (EEG) of a patient under sedation after anesthesia administration is depicted in FIG. 4.

While specific embodiments of the present inventive concept have been shown and described, it will be understood that other modifications, substitutions and alternatives are apparent to one of ordinary skill in the art. Such modifications, substitutions and alternatives can be made without departing from the spirit and scope of the inventive concept, which should be determined from the appended claims.

That which is claimed:

1. A method for reducing neuronal agitation and cellular oxygenation deficiencies in a subject in need thereof comprising administering a therapeutic amount of Dobutamine to improve microvasculature transport of bloodflow.

2. The method of claim 1, wherein the Dobutamine is delivered intravenously.

3. The method of claim 1, wherein the Dobutamine is delivered via injection.

4. The method of claim 1, wherein the Dobutamine is delivered via an ingestible formulation.

5. The method of claim 1, wherein the subject is a human subject.

6. The method of claim 5, wherein the human subject is a neonate, infant, juvenile, or adolescent human subject.

7. The method of claim 5, wherein the human subject is an adult.

8. The method of claim 1, wherein reducing neuronal agitation and cellular oxygenation deficiencies in the subject further comprises:
   medically sedating the subject for a sustained period of time by administering a therapeutically effective amount of an anesthetic,
   wherein sedating the subject pauses bioelectrical activity of neurons in the subject to facilitate healing of the neurons in the subject.

9. The method of claim 8, wherein the pausing of bioelectrical activity is monitored by an electroencephalogram (EEG) and/or by functional magnetic resonance imaging (fMRI).

10. The method of claim 1, wherein the reducing of neuronal agitation and cellular oxygen deficiencies is for treating a neurological dysfunction selected from the group consisting of: Epilepsy; seizures; Infantile Spasms; Essential Tremors; Essential Palatal Tremors; Hemiplegia; Parkinson's; Blepharospasms; Nystagmus; Mènière; Fibromyalgia; Multiple Sclerosis; Longevity; Myalgic Encephalomyelitis (Chronic Fatigue Syndrome); Guillain-Barre Syndrome; Chronic Inflammatory Demyelinating Polyneuropathy; Amyotrophic Lateral Sclerosis; Cluster and Migraine Headaches; Peripheral Pain; Restless Leg Syndrome; Phantom-limb Pain; Myasthenia Gravis; Rett Syndrome; Mitochondrial Disease; GLUT1 Deficiency Syndrome; Pyruvate Dehydrogenase Complex Deficiency; Spinal Axonal Repair; Spinal Surgery Recovery; Hippocampal Memory Retrieval Deficits; Lewy body Dementia;

Attention Deficit Disorder and Attention Deficit Hyperactivity Disorder; Autism and Asperger's; Depression; Post-Traumatic Stress Disorders; Chronic Anxiety; Nightmares and disruptive sleep disorders; Impulsivity; Compulsivity; Inattentiveness; Addictive Soothing Behaviors; Anorexia Nervosa; a Chemical Addiction selected from the group consisting of Alcohol addiction, Opioid addiction, Nicotine addiction, and Methamphetamine addiction; Human alcohol-related neuropathology; Dementia; Alzheimer's; Schizophrenia; Bipolar Disorder; Obsessive-Compulsive Disorder; Psychosis; Auditory Agnosia; Hyperacusis; Tinnitus; Auditory Neuropathy; Stuttering of Speech; Speech Tics; Tourette's; Cerebral Palsy; Acute Respiratory Distress Syndrome; Neuromuscular Disorders; Seizures from Neurosurgery; Benign Rolandic Epilepsy of Childhood; Benign Familial Neonatal Infantile Seizures; Absence Epilepsy; Juvenile Myoclonic Epilepsy; Benign Occipital Epilepsy; Lennox-Gastaut Syndrome Epilepsy; SCN2A encephalopathy; Myoclonic Astatic Epilepsy; and Narcolepsy.

11. A method for enabling remyelination and neurological repairs in a subject in need thereof comprising:
medically sedating the subject for a minimum of three days by administering a therapeutically effective amount of an anesthetic,
wherein medically sedating the subject pauses bioelectrical activity of neurons in the subject to facilitate systemic repair of the neurons in the subject.

12. The method of claim 11, wherein the anesthetic is midazolam, or a pharmaceutically acceptable salt thereof.

13. The method of claim 11, wherein the subject is further administered a medication to induce vasodilation, oxygenation, and/or reduction of inflammation in the subject prior to, during, and/or after medical sedation.

14. The method of claim 13, wherein the medication to induce vasodilation, oxygenation, and/or reduction of inflammation is Dobutamine.

15. The method of claim 11, wherein the subject is a human subject.

16. The method of claim 15, wherein the human subject is a neonate, infant, juvenile, or adolescent human subject.

17. The method of claim 15, wherein the human subject is an adult.

18. The method of claim 11, wherein the pausing of bioelectrical activity is monitored by an electroencephalogram (EEG) and/or by functional magnetic resonance imaging (fMRI).

19. The method of claim 11, wherein enabling remyelination and neurological repairs in the subject is for treating a neurological dysfunction selected from the group consisting of: Epilepsy; seizures; Infantile Spasms; Essential Tremors; Essential Palatal Tremors; Hemiplegia; Parkinson's; Blepharospasms; Nystagmus; Mènière; Fibromyalgia; Multiple Sclerosis; Longevity; Myalgic Encephalomyelitis (Chronic Fatigue Syndrome); Guillain-Barre Syndrome; Chronic Inflammatory Demyelinating Polyneuropathy; Amyotrophic Lateral Sclerosis; Cluster and Migraine Headaches; Peripheral Pain; Restless Leg Syndrome; Phantom-limb Pain; Myasthenia Gravis; Rett Syndrome; Mitochondrial Disease; GLUT1 Deficiency Syndrome; Pyruvate Dehydrogenase Complex Deficiency; Spinal Axonal Repair; Spinal Surgery Recovery; Hippocampal Memory Retrieval Deficits; Lewy body Dementia; Attention Deficit Disorder and Attention Deficit Hyperactivity Disorder; Autism and Asperger's; Depression; Post-Traumatic Stress Disorders; Chronic Anxiety; Nightmares and disruptive sleep disorders; Impulsivity; Compulsivity; Inattentiveness; Addictive Soothing Behaviors; Anorexia Nervosa; a Chemical Addiction selected from the group consisting of Alcohol addiction, Opioid addiction, Nicotine addiction, and Methamphetamine addiction; Human alcohol-related neuropathology; Dementia; Alzheimer's; Schizophrenia; Bipolar Disorder; Obsessive-Compulsive Disorder; Psychosis; Auditory Agnosia; Hyperacusis; Tinnitus; Auditory Neuropathy; Stuttering of Speech; Speech Tics; Tourette's; Cerebral Palsy; Acute Respiratory Distress Syndrome; Neuromuscular Disorders; Seizures from Neurosurgery; Benign Rolandic Epilepsy of Childhood; Benign Familial Neonatal Infantile Seizures; Absence Epilepsy; Juvenile Myoclonic Epilepsy; Benign Occipital Epilepsy; Lennox-Gastaut Syndrome Epilepsy; SCN2A encephalopathy; Myoclonic Astatic Epilepsy; and Narcolepsy.

\* \* \* \* \*

UNITED STATES PATENT AND TRADEMARK OFFICE
CERTIFICATE OF CORRECTION

PATENT NO. : 11,446,262 B2
APPLICATION NO. : 16/935064
DATED : September 20, 2022
INVENTOR(S) : Debora Zucco Sassi Yonezawa Siviglia and Gary Aaron Howard It is certified that error appears in the above-identified patent and that said Letters Patent is hereby corrected as shown below:

On the Title Page

Item (56) References, Other Publications, Page 2, Left Column, Ma cite: Please correct "Olig2/LING0-1" to read -- Olig2/LINGO-1 --

Other Publications, Page 2, Right Column, Yuan cite: Please correct "by Cherriogenetic" to read -- by Chemogenetic --

In the Specification

Columns 17-18, Midazolam Deep Quiet Chart, Heading: Body Weight, Line: 50 kg, Heading: Day Three of Sedation: Please correct "5.0 mL per hour" to read -- 6.0 mL per hour --

In the Claims

Column 28, Claim 10, Line 57: Please correct "Nystagmus;"Mènière;" to read -- Nystagmus; Ménière; --

Column 30, Claim 19, Line 10: Please correct "Nystagmus;"Mènière;" to read -- Nystagmus; Ménière; --

Signed and Sealed this
Twenty-ninth Day of November, 2022

Katherine Kelly Vidal
*Director of the United States Patent and Trademark Office*